(12) United States Patent
Shinoda et al.

(10) Patent No.: US 10,395,367 B2
(45) Date of Patent: Aug. 27, 2019

(54) MAGNETIC RESONANCE IMAGING APPARATUS

(71) Applicant: TOSHIBA MEDICAL SYSTEMS CORPORATION, Otawara-shi (JP)

(72) Inventors: Kensuke Shinoda, Tochigi (JP); Yasuo Sakurai, Tochigi (JP); Yuichi Yamashita, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 0 days.

(21) Appl. No.: 14/943,699

(22) Filed: Nov. 17, 2015

(65) Prior Publication Data

US 2016/0071270 A1    Mar. 10, 2016

Related U.S. Application Data

(63) Continuation of application No. PCT/JP2014/062530, filed on May 9, 2014.

(30) Foreign Application Priority Data

May 20, 2013 (JP) ................................ 2013-106293

(51) Int. Cl.
G06T 7/00         (2017.01)
A61B 5/055        (2006.01)
(Continued)

(52) U.S. Cl.
CPC ............ *G06T 7/0014* (2013.01); *A61B 5/055* (2013.01); *A61B 5/4566* (2013.01);
(Continued)

(58) Field of Classification Search
CPC combination set(s) only.
See application file for complete search history.

(56) References Cited

U.S. PATENT DOCUMENTS 5,291,537 A * 3/1994 Mazess ................. A61B 6/032
                                                    378/54
5,931,780 A * 8/1999 Giger .................... A61B 6/482
                                                    600/407
(Continued)

FOREIGN PATENT DOCUMENTS

JP           6-22933      2/1994
JP         2005-237968    9/2005
(Continued)

OTHER PUBLICATIONS

International Search Report for PCT/JP2014/062530 (JP language), dated Jul. 15, 2014, 4 pages.
(Continued)

*Primary Examiner* — Anand P Bhatnagar
(74) *Attorney, Agent, or Firm* — Nixon & Vanderhye P.C.

(57) ABSTRACT

A magnetic resonance imaging apparatus according to embodiments includes processing circuitry. The processing circuitry is configured to detect, defining at least either intervertebral discs or vertebral bodies as target regions, target region information indicative of a position and a direction of each target region for each of a plurality of target regions included in a spine of a subject based on an image in which the spine is imaged; select target regions of imaging subjects out of the target regions based on the target region information; and cause a display to display, regarding the target regions, information representing imaging areas that concern the target regions of imaging subjects and information representing imaging areas that concern other target regions in different display forms.

16 Claims, 15 Drawing Sheets

(51) Int. Cl.
   *A61B 5/00*    (2006.01)
   *G01R 33/483*  (2006.01)
   *G01R 33/56*   (2006.01)
   *G06T 11/00*   (2006.01)
   *G01R 33/54*   (2006.01)
   *G06T 7/11*    (2017.01)

(52) U.S. Cl.
   CPC ....... *G01R 33/4835* (2013.01); *G01R 33/546* (2013.01); *G01R 33/5608* (2013.01); *G06T 7/11* (2017.01); *G06T 11/003* (2013.01); *G06T 2207/10088* (2013.01); *G06T 2207/20104* (2013.01); *G06T 2207/30012* (2013.01)

(56) References Cited

U.S. PATENT DOCUMENTS

| | | | | |
|---|---|---|---|---|
| 7,548,638 | B2 | 6/2009 | Graessner | |
| 7,570,791 | B2* | 8/2009 | Frank | A61B 6/4441 |
| | | | | 382/128 |
| 8,384,735 | B2* | 2/2013 | Wang | G06F 19/321 |
| | | | | 345/619 |
| 8,568,331 | B2* | 10/2013 | Bertagnoli | A61B 5/4041 |
| | | | | 600/554 |
| 8,729,896 | B2* | 5/2014 | Ohmure | G01R 33/48 |
| | | | | 324/307 |
| 9,754,369 | B2* | 9/2017 | Weiss | B60R 25/00 |
| 2003/0086596 | A1* | 5/2003 | Hipp | G06T 7/0012 |
| | | | | 382/128 |
| 2006/0085068 | A1* | 4/2006 | Barry | A61B 17/1615 |
| | | | | 623/17.11 |
| 2008/0260226 | A1 | 10/2008 | Moriya | |
| 2009/0290771 | A1* | 11/2009 | Frank | A61B 6/4441 |
| | | | | 382/128 |
| 2012/0053454 | A1* | 3/2012 | Wang | A61B 6/463 |
| | | | | 600/425 |
| 2012/0143090 | A1* | 6/2012 | Hay | A61B 6/505 |
| | | | | 600/587 |
| 2013/0173240 | A1* | 7/2013 | Koell | G06F 17/5009 |
| | | | | 703/2 |
| 2013/0322727 | A1* | 12/2013 | Goto | G06T 1/0007 |
| | | | | 382/132 |
| 2014/0132268 | A1* | 5/2014 | Nagao | A61B 5/055 |
| | | | | 324/321 |
| 2015/0260814 | A1 | 9/2015 | Sakurai et al. | |

FOREIGN PATENT DOCUMENTS

| | | |
|---|---|---|
| JP | 2006-129937 | 5/2006 |
| JP | 2006-320527 A | 11/2006 |
| JP | 2009-95644 | 5/2009 |
| JP | 2012-045192 | 3/2012 |
| WO | WO 2012/176886 | 12/2012 |
| WO | WO 2014/081023 | 5/2014 |

OTHER PUBLICATIONS

Written Opinion of the ISA for PCT/JP2014/062530 (JP language), dated Jul. 15, 2014, 5 pages.
JP Office Action dated Aug. 16, 2016 in JP 2013-106293.
Japanese office action dated Oct. 9, 2018, in Patent Application No. JP 2017-209615.

* cited by examiner

MAGNETIC RESONANCE IMAGING APPARATUS

CROSS-REFERENCE TO RELATED APPLICATIONS

This application is a continuation of PCT international application Ser. No. PCT/JP2014/062530 filed on May 9, 2014 which designates the United States, incorporated herein by reference, and which claims the benefit of priority from Japanese Patent Application No. 2013-106293, filed on May 20, 2013, the entire contents of which are incorporated herein by reference.

FIELD

Embodiments described herein relate generally to a magnetic resonance imaging apparatus.

BACKGROUND

Conventionally, in an examination of intervertebral discs using a magnetic resonance imaging apparatus, a cross-sectional image that is parallel to the intervertebral discs and includes the intervertebral discs is imaged. In such an examination, a method is known in which, for example, the magnetic resonance imaging apparatus automatically detects a plurality of intervertebral discs from an image in which the spine of a subject is imaged and defines imaging areas to the respective intervertebral discs. A method that detects a plurality of vertebral bodies and defines imaging areas to the respective vertebral bodies is also known. In the examinations using these methods, in general, after at least either the intervertebral discs or the vertebral bodies are detected as target regions, an operator selects, out of the detected target regions, as many target regions intended to be imaging subjects as the number corresponding to an imaging protocol. Examples are described in Japanese Patent Application Laid-open No. 2012-045192 and Japanese Patent Application Laid-open No. 2005-237968.

DETAILED DESCRIPTION

A magnetic resonance imaging apparatus according to embodiments includes processing circuitry. The processing circuitry is configured to detect, defining at least either intervertebral discs or vertebral bodies as target regions, target region information indicative of a position and a direction of each target region for each of a plurality of target regions included in a spine of a subject based on an image in which the spine is imaged; select target regions of imaging subjects out of the target regions based on the target region information; and cause a display to display, regarding the target regions, information representing imaging areas that concern the target regions of imaging subjects and information representing imaging areas that concern other target regions in different display forms.

With reference to the accompanying drawings, the following describes in detail MRI apparatuses according to exemplary embodiments.

First Embodiment

Figure 1:
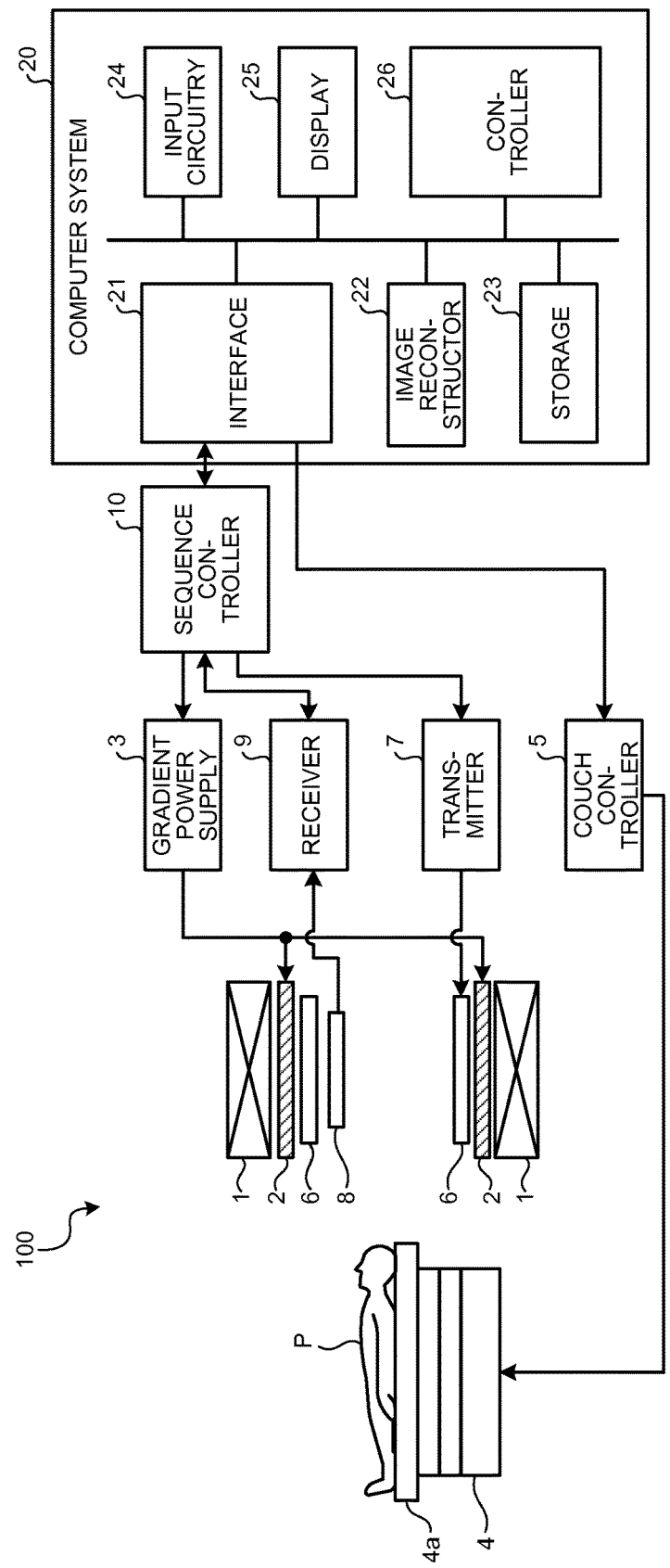
FIG. 1 is a block diagram illustrating the configuration of an MRI apparatus according to a first embodiment.

FIG. 1 is a block diagram illustrating the configuration of an MRI apparatus according to a first embodiment. As illustrated in FIG. 1, an MRI apparatus 100 includes a static magnet 1, a gradient coil 2, a gradient power supply 3, a couch 4, a couch controller 5, a transmitting RF coil 6, a transmitter 7, a receiving RF coil 8, a receiver 9, a sequence controller 10, and a computer system 20.

The static magnet 1 is a magnet formed in a hollow cylindrical shape, and in the inner void space thereof, generates a uniform static magnetic field. As for the static magnet 1, a permanent magnet and a superconducting magnet are used, for example.

The gradient coil 2 is a coil formed in a hollow cylindrical shape and is disposed on the inner side of the static magnet 1. The gradient coil 2 is formed with a combination of three coils corresponding to respective axes of x, y, and z which are orthogonal to one another. The three coils each receive a supply of current individually from the gradient power supply 3 which will be described later, and generate a gradient magnetic field the magnetic field intensity of which varies along the respective axes of x, y, and z. The direction of the z axis is defined identical to that of the static magnetic field. The gradient power supply 3 supplies the current to the gradient coil 2.

The gradient magnetic fields on the respective axes of x, y, and z generated by the gradient coil 2 correspond to a slice-selecting gradient magnetic field Gss, a phase-encoding gradient magnetic field Gpe, and a read-out gradient magnetic field Gro, respectively, for example. The slice-selecting gradient magnetic field Gss is used to determine any desired imaging cross-section. The phase-encoding gradient magnetic field Gpe is used to alter the phase of a magnetic resonance signal depending on a spatial location. The read-out gradient magnetic field Gro is used to alter the frequency of the magnetic resonance signal depending on the spatial location.

The couch 4 includes a couchtop 4a on which a subject P is placed, and under the control of the couch controller 5 which will be described later, inserts the couchtop 4a, in a state of the subject P being placed thereon, into a cavity (imaging opening) of the gradient coil 2. Normally, the couch 4 is installed such that the longitudinal direction thereof is in parallel with the central axis of the static magnet 1. The couch controller 5 is a device that controls the couch 4 under the control of a controller 26, and drives the couch 4 to move the couchtop 4a in the longitudinal direction and up-and-down direction thereof.

The transmitting RF coil 6 is disposed on the inner side of the gradient coil 2, and with high-frequency pulse current supplied from the transmitter 7, generates a radio frequency (RF) pulse (high-frequency magnetic field pulse). The transmitter 7 supplies the high-frequency pulse current corresponding to a Larmor frequency to the transmitting RF coil 6. The receiving RF coil 8 is disposed on the inner side of the gradient coil 2 and receives a magnetic resonance signal emitted from the subject P by the influence of the above-described RF pulse. The receiving RF coil 8, upon receiving the magnetic resonance signal, outputs the magnetic resonance signal to the receiver 9.

The receiver 9 generates magnetic resonance (MR) signal data based on the magnetic resonance signal output from the receiving RF coil 8. The receiver 9 generates the MR signal data by performing digital conversion on the magnetic resonance signal output from the receiving RF coil 8. The MR signal data is associated with information on spatial frequency in a phase-encode direction, a read-out direction, and a slice-encode direction, by the foregoing slice-selecting gradient magnetic field Gss, the phase-encoding gradient magnetic field Gpe, and the read-out gradient magnetic field Gro, respectively, and is disposed in k-space. The receiver 9, upon generating the MR signal data, sends the MR signal data to the sequence controller 10.

The sequence controller 10 drives the gradient power supply 3, the transmitter 7, and the receiver 9 based on sequence execution data transmitted from the computer system 20, and thereby executes scans of the subject P. The sequence execution data here is the information in which a pulse sequence indicative of a procedure to execute scans of the subject P, such as the strength of and the timing of power supply that the gradient power supply 3 supplies to the gradient coil 2, the intensity of and the timing of an RF signal that the transmitter 7 transmits to the transmitting RF coil 6, and the timing that the receiver 9 detects a magnetic resonance signal, is defined. The sequence controller 10, after driving the gradient power supply 3, the transmitter 7, and the receiver 9 based on the sequence execution data, and when MR signal data is transmitted from the receiver 9, transfers the MR signal data to the computer system 20.

The computer system 20 performs overall control of the MRI apparatus 100. For example, the computer system 20 drives various modules the MRI apparatus 100 includes, and thereby performs scans of the subject P, reconstruction of images, and others. The computer system 20 includes an interface 21, an image reconstructor 22, a storage 23, an input circuitry 24, a display 25, and the controller 26.

The interface 21 controls the input and output of various signals exchanged with the sequence controller 10. For example, the interface 21 transmits sequence execution data to the sequence controller 10 and receives MR signal data from the sequence controller 10. Upon receiving the MR signal data, the interface 21 causes respective pieces of MR signal data to be stored in the storage 23 for each subject P.

The image reconstructor 22 performs post-processing, that is, reconstruction processing such as Fourier transformation, on the MR signal data stored in the storage 23, and thereby generates spectrum data of or image data of desired nuclear spins inside the subject P. Furthermore, the image reconstructor 22 causes the generated spectrum data or image data to be stored in the storage 23 for each subject P.

The storage 23 stores therein a variety of data and various programs necessary for the processing executed by the controller 26 which will be described later. For example, the storage 23 stores therein the MR signal data received by the interface 21, the spectrum data and the image data generated by the image reconstructor 22, and others, for each subject P. The storage 23 is a semiconductor memory device such as a random access memory (RAM), a read only memory (ROM), and a flash memory, and a storage device such as a hard disk and an optical disc, for example.

The input circuitry 24 receives various instructions and information inputs from an operator. As for the input circuitry 24, a pointing device such as a mouse and a trackball, a select device such as a mode-select switch, or an input device such as a keyboard can be used as appropriate.

The display 25 displays, under the control of the controller 26, a variety of information such as spectrum data or image data. As for the display 25, a display device such as a liquid crystal display can be used.

The controller 26 includes a central processing unit (CPU), a memory, and others not depicted, and performs the overall control of the MRI apparatus 100. The controller 26 generates various sequence execution data based on an imaging condition received from the operator via the input circuitry 24 and transmits the generated sequence execution data to the sequence controller 10, and thereby controls scans, for example. Furthermore, when the MR signal data is transmitted from the sequence controller 10 as a result of the scans, the controller 26 controls the image reconstructor 22 so as to reconstruct an image based on the MR signal data.

The configuration of the MRI apparatus 100 has been explained in the foregoing. With such a configuration, the MRI apparatus 100 has a function to detect a plurality of intervertebral discs from an image in which the spine of a subject is imaged. Conventionally, in such automatic detection of intervertebral discs, all of the intervertebral discs included in an image have been detected. This has caused the imaging time and examination time to be prolonged unless the number of intervertebral discs to be imaging subjects is narrowed down. Consequently, in general, after the intervertebral discs are detected, the operator has selected, out of the detected intervertebral discs, as many intervertebral discs intended to be the imaging subjects as the number corresponding to an imaging protocol.

Meanwhile, the MRI apparatus 100 in the first embodiment selects intervertebral discs of imaging subjects out of a plurality of detected intervertebral discs, and causes the information representing the imaging areas that concern the intervertebral discs of imaging subjects and the information representing the imaging areas that concern the other intervertebral discs to be displayed in different display forms. This enables the operator to easily select the intervertebral discs intended to be the imaging subjects. The following explains in detail such an MRI apparatus 100.

Figure 2:
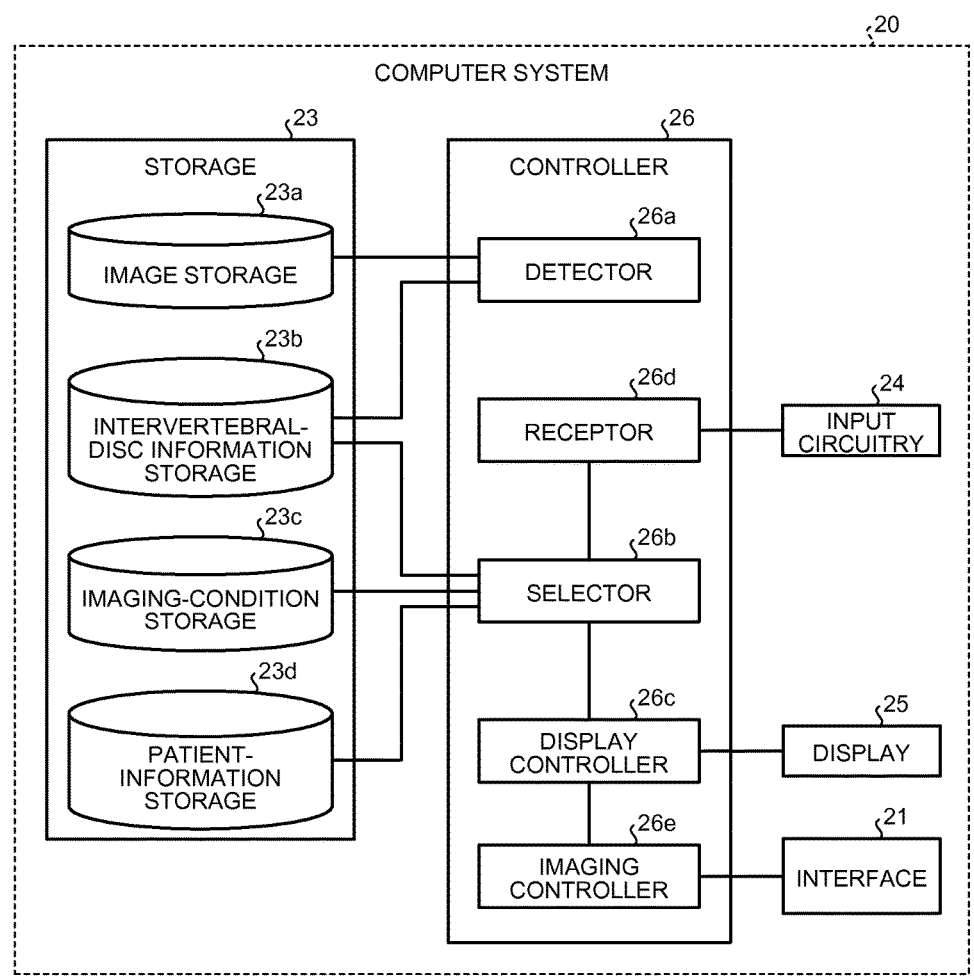
FIG. 2 is a functional block diagram illustrating the detailed configuration of the MRI apparatus in the first embodiment.

FIG. 2 is a functional block diagram illustrating the detailed configuration of the MRI apparatus 100 in the first embodiment. In FIG. 2, illustrated are, out of a variety of elements that the computer system 20 illustrated in FIG. 1 includes, the interface 21, the storage 23, the input circuitry 24, the display 25, and the controller 26.

As illustrated in FIG. 2, the storage 23 includes an image storage 23a, an intervertebral-disc information storage 23b, an imaging-condition storage 23c, and a patient-information storage 23d.

The image storage 23a stores therein image data generated by the image reconstructor 22. In the first embodiment, the image storage 23a stores therein at least positioning sagittal images in which the spine of a subject is imaged. For example, the positioning sagittal image is a sagittal image that is parallel to a sagittal cross-section including the intervertebral discs and the vertebral canal of the subject and includes at least the intervertebral discs. This positioning sagittal image is imaged by a sequence that can image the intervertebral discs at higher signal values than the vertebral bodies such as a field echo (FE) based sequence, for example.

The intervertebral-disc information storage 23b stores therein intervertebral disc information that is detected from an image in which the spine of a subject is imaged. In the first embodiment, the intervertebral-disc information storage 23b stores therein the intervertebral disc information detected from the positioning sagittal images that are stored in the image storage 23a. The intervertebral disc information here is the information indicative of the position and direction of an intervertebral disc, and is indicated by a first vector that represents the direction of the intervertebral disc, and a coordinate that represents the position of origin of the first vector, or a second vector (a vector based on a predetermined reference position as the origin), for example.

The imaging-condition storage 23c stores therein imaging conditions that concern various imaging methods and various pulse sequences for each imaging protocol. The imaging condition here includes imaging parameters such as a repetition time (TR); an echo time (TE); the number of matrices; the length, width, and thickness of an imaging area; and the number of slices within the imaging area. The imaging condition further includes imaging methods (types of pulse sequence such as spin-echo method, and echo planar imaging (EPI) method); the type, number, and order of pre-pulse such as fat suppressing pulse and inversion pulse; and the order of imaging the imaging areas. The imaging condition further includes the number of intervertebral discs to be the imaging subjects when the intervertebral discs are imaged. The imaging area that includes a plurality of slices is also referred to as a slice group or a slab.

The patient-information storage 23d stores therein patient information that concerns a subject. The patient information here means the identification information, name, age, body height, and body weight of the subject, for example.

The controller 26 includes a detector 26a, a selector 26b, a display controller 26c, a receptor 26d, and an imaging controller 26e.

The detector 26a detects, based on an image in which the spine of a subject is imaged, the intervertebral disc information indicative of the position and direction of each intervertebral disc for each of a plurality of intervertebral discs. In the first embodiment, the detector 26a detects the intervertebral disc information based on positioning sagittal images stored in the image storage 23a. The detector 26a then causes the intervertebral-disc information storage 23b to store therein the detected intervertebral disc information. As for the detection method of intervertebral discs that the detector 26a uses, various methods can be employed.

For example, the detector 26a detects the intervertebral disc information by a method using a plurality of sagittal images of a subject. In this method, the detector 26a extracts a spine area from each of a plurality of sagittal images that are parallel to a sagittal cross-section including the intervertebral discs and vertebral canal of the subject and include at least the intervertebral discs. The detector 26a further extracts a two-dimensional intervertebral disc area from each of a plurality of detected spine areas. The detector 26a then extracts, based on the extracted two-dimensional intervertebral disc areas, a three-dimensional intervertebral disc area extending over the sagittal images.

The selector 26b selects, based on the intervertebral disc information detected by the detector 26a, the intervertebral discs of imaging subjects out of a plurality of intervertebral discs. In the first embodiment, the selector 26b selects as many intervertebral discs of imaging subjects as intervertebral discs stored by the imaging-condition storage 23c. For example, the selector 26b selects, from the upper side (head side), as many intervertebral discs as intervertebral discs stored by the imaging-condition storage 23c out of a plurality of intervertebral discs included in a positioning sagittal image based on the intervertebral disc information detected by the detector 26a. Alternatively, the selector 26b may select the intervertebral discs from the lower side (foot side) out of a plurality of intervertebral discs or may select the intervertebral discs from near the middle out of a plurality of intervertebral discs. Furthermore, the selector 26b newly selects the intervertebral discs of imaging subjects in response to a selection operation received by the receptor 26d which will be described later.

The display controller 26c controls to display, regarding a plurality of intervertebral discs for which the intervertebral disc information has been detected by the detector 26a, the information representing the imaging areas that concern the intervertebral discs of imaging subjects selected by the selector 26b and the information representing the imaging areas that concern the other intervertebral discs in different display forms, on the display 25. That is, the display controller 26c controls the display 25 to distinctly display the imaging areas that concern the intervertebral discs of imaging subjects, and the imaging areas that concern the intervertebral discs that are not the imaging subjects.

Figure 3:
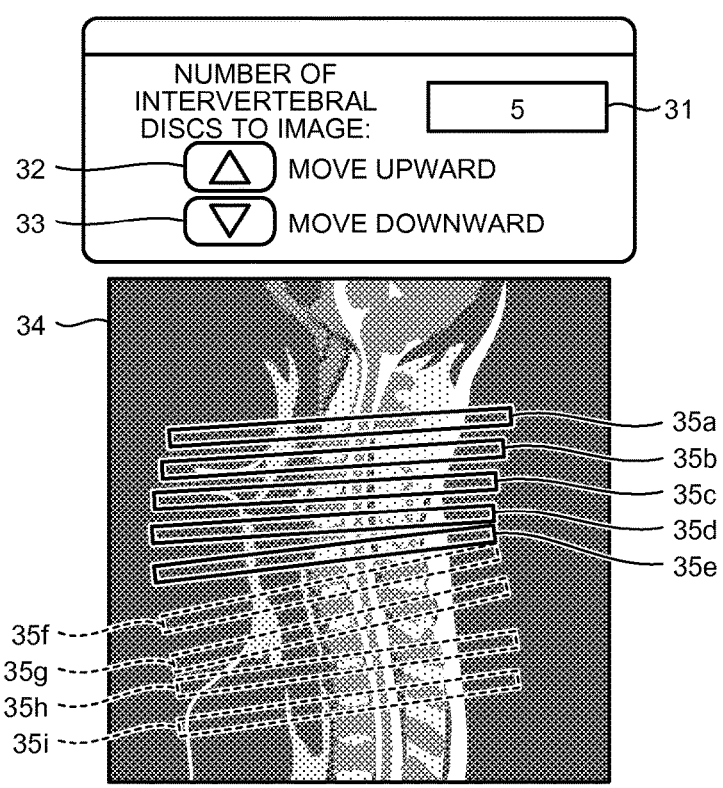
FIG. 3 is a diagram illustrating one example of the display of imaging areas performed by a display controller in the first embodiment.

FIG. 3 is a diagram illustrating one example of the display of imaging areas performed by the display controller 26c in the first embodiment. For example, as illustrated in FIG. 3, the display controller 26c controls to display a text box 31 that displays the number of intervertebral discs of imaging subjects, a button 32 that receives an instruction to move the intervertebral discs of imaging subjects upward, a button 33 that receives an instruction to move the intervertebral discs of imaging subjects downward, and a positioning sagittal image 34. The display controller 26c acquires the number of intervertebral discs stored by the imaging-condition storage 23c and controls to display the acquired number of intervertebral discs in the text box 31.

The display controller 26c further controls to display imaging areas that concern the respective intervertebral discs with rectangular graphics on the positioning sagittal image 34. Such graphics are also referred to as region of interest (ROI). In FIG. 3, illustrated is an example of a situation that the number of intervertebral discs is five. In this case, the display controller 26c controls to display, out of a plurality of intervertebral discs, graphics 35a to 35e that concern the intervertebral discs of imaging subjects and graphics 35f to 35i that concern the other intervertebral discs that are not the imaging subjects in different display forms, for example. At this time, display controller 26c may alter the color of the graphics, or may alter the line width and line style (such as solid lines and dotted lines) thereof, for example.

The imaging controller 26e controls the sequence controller 10 so as to collect the data of imaging areas that concern the intervertebral discs of imaging subjects selected by the selector 26b. Specifically, the imaging controller 26e generates sequence execution data to collect the data of imaging areas that concern the selected intervertebral discs of imaging subjects based on the imaging condition stored in the imaging-condition storage 23c, and transmits the generated sequence execution data to the sequence controller 10.

The receptor 26d receives a selection operation that selects the intervertebral discs of imaging subjects from the operator. Specifically, the receptor 26d receives, via the input circuitry 24, an operation of selecting the information indicative of imaging areas that concern the intervertebral discs displayed on the display 25. For example, the receptor 26d receives an operation of specifying one direction or the other direction along the disposed direction of a plurality of intervertebral discs, as a selection operation that selects the intervertebral discs of imaging subjects.

In this case, when a selection operation is received by the receptor 26d, the selector 26b newly selects the intervertebral discs of imaging subjects of the same number as that of intervertebral discs of imaging subjects having been selected before the selection operation is received, including the intervertebral disc positioned on the side of the direction specified by the selection operation with respect to the intervertebral discs having been selected as the imaging subjects before the selection operation is received, toward the opposite side to the direction specified by the selection operation, for example. That is, the selector 26b moves the intervertebral discs of imaging subjects along the disposed direction of the intervertebral discs within the intervertebral discs detected by the detector 26a while keeping the number of intervertebral discs first selected as the imaging subjects. When the intervertebral discs of imaging subjects are changed by the selector 26b, the display controller 26c then alters the display forms of the graphics that concern the respective intervertebral discs in response to the change.

Figure 4:
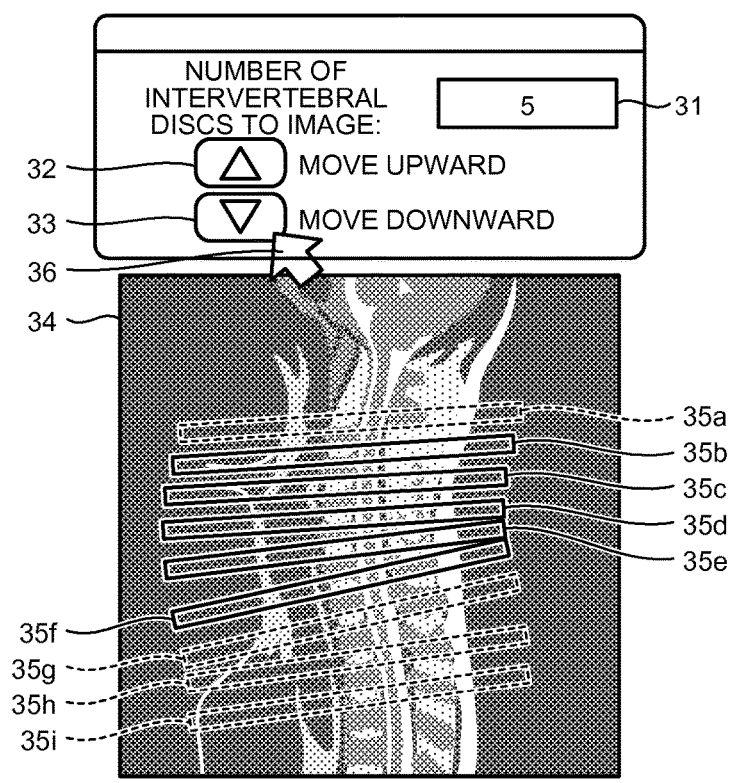
FIG. 4 is a diagram for explaining the re-selection of intervertebral discs performed by a receptor and a selector in the first embodiment.

FIG. 4 is a diagram for explaining the re-selection of intervertebral discs performed by the receptor 26d and the selector 26b in the first embodiment. The text box 31, the buttons 32 and 33, the positioning sagittal image 34, and the graphics 35a to 35i illustrated in FIG. 4 are the same as those illustrated in FIG. 3. For example, as illustrated in FIG. 4, the receptor 26d receives an operation of specifying the button 32 or 33 displayed on the display 25 with a mouse pointer 36 and the like.

As illustrated in FIG. 4, when the button 33 (move downward) is specified in a state illustrated in FIG. 3, the selector 26b newly selects, toward the upper side, only five intervertebral discs of imaging subjects, which is the same as the number of intervertebral discs having been selected as the imaging subjects before the button 33 is specified, including the intervertebral disc corresponding to the graphic 35f positioned immediately below the intervertebral discs corresponding to the graphics 35a to 35e having been selected as the imaging subjects before the button 33 is specified, for example. As a result of this, as illustrated in FIG. 4, the respective intervertebral discs corresponding to the graphics 35b to 35f are newly selected as the imaging subjects. Along with this, the display controller 26c then controls to display, in display forms indicative of being the imaging subjects, the graphics 35b to 35f that concern the newly selected intervertebral discs as the imaging subjects, and controls to display, in display forms indicative of not being the imaging subjects, the graphic 35a and the graphics 35g to 35i that concern the other intervertebral discs. The selector 26b and the display controller 26c perform the same processing each time the button 33 is specified by the operator. Consequently, each time the button 33 is specified by the operator, the intervertebral discs selected as the subject of selection are to move downward while keeping the number thereof constant.

Meanwhile, when the button 32 (move upward) is specified in a state illustrated in FIG. 4, the selector 26b newly selects, toward the upper side, only five intervertebral discs, which is the same as the number of intervertebral discs of imaging subjects having been selected as the imaging subjects before the button 32 is specified, including the intervertebral disc corresponding to the graphic 35a positioned immediately above the intervertebral discs corresponding to the graphics 35b to 35f having been selected as the imaging subjects before the button 32 is specified, for example. As a result of this, the respective intervertebral discs corresponding to the graphics 35a to 35e are newly selected as the imaging subjects. Along with this, the display controller 26c then controls to display, in display forms indicative of being the imaging subjects, the graphics 35a to 35e that concern the newly selected intervertebral discs as the imaging subjects, and controls to display, in display forms indicative of not being the imaging subjects, the graphics 35f to 35i that concern the other intervertebral discs. The selector 26b and the display controller 26c perform the same processing each time the button 32 is specified by the operator. Consequently, each time the button 32 is specified by the operator, the intervertebral discs selected as the subject of selection are to move upward while keeping the number thereof constant.

As in the foregoing, in the first embodiment, the receptor 26d receives a selection operation that selects the intervertebral discs of imaging subjects from the operator, and the selector 26b newly selects the intervertebral discs of imaging subjects in response to the selection operation received by the receptor 26d. Consequently, the operator can select the intervertebral discs anew after the intervertebral discs are selected by the selector 26b. Because the same number of intervertebral discs are selected even when the intervertebral discs of imaging subjects are re-selected again, the intervertebral discs can be re-selected while keeping the imaging time.

Figure 5:
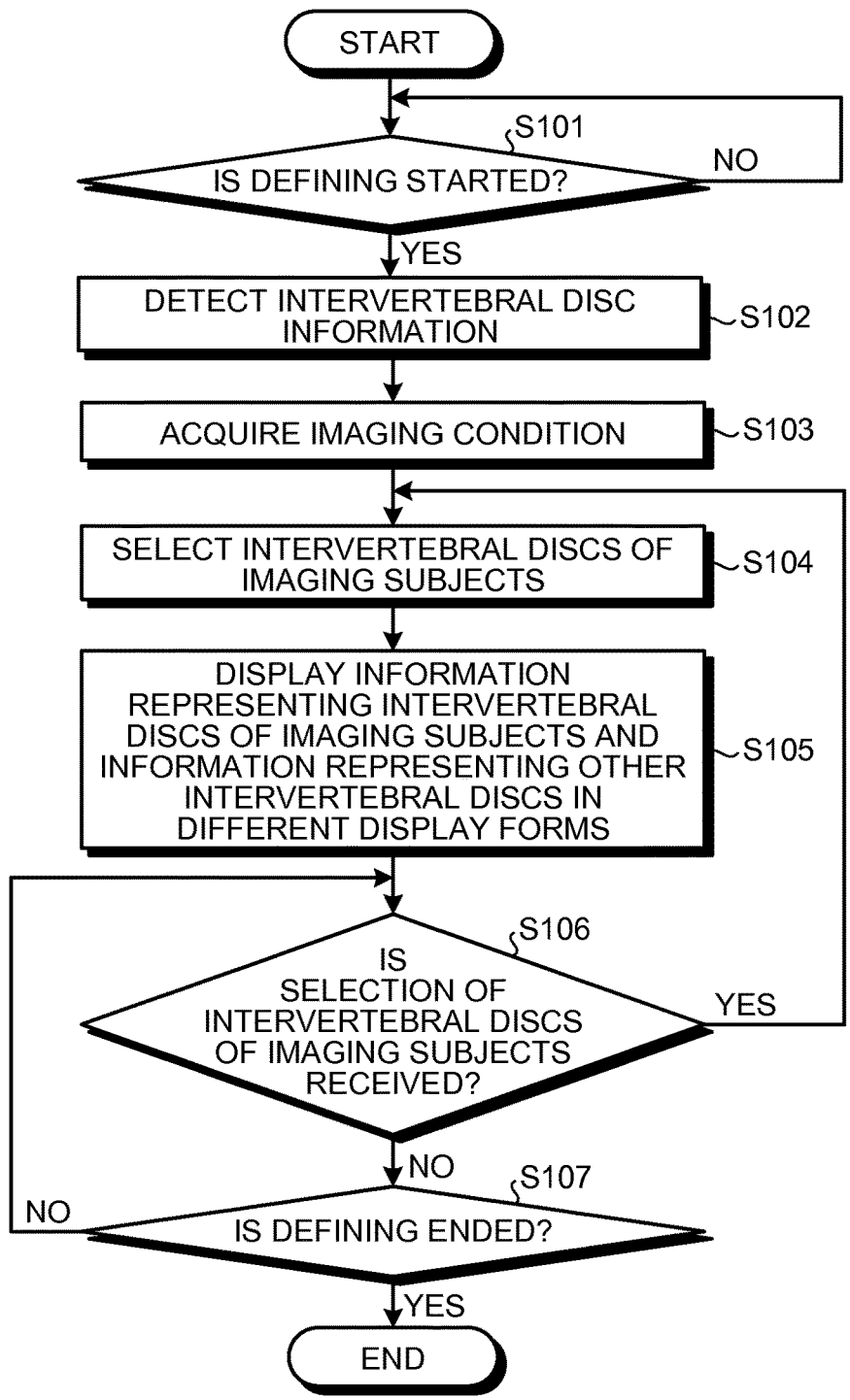
FIG. 5 is a flowchart illustrating a processing procedure of an imaging-area defining method performed by the MRI apparatus in the first embodiment.

FIG. 5 is a flowchart illustrating a processing procedure of an imaging-area defining method performed by the MRI apparatus 100 in the first embodiment. As illustrated in FIG. 5, in the MRI apparatus 100 in the first embodiment, the controller 26 starts the following processing when an instruction to start defining imaging areas is received from the operator (Yes at Step S101).

The detector 26a first detects, based on an image in which the spine of a subject is imaged, the intervertebral disc information indicative of the position and direction of each intervertebral disc for each of a plurality of intervertebral discs (Step S102). Thereafter, the selector 26b acquires an imaging condition stored by the imaging-condition storage 23c (Step S103), and selects as many intervertebral discs of imaging subjects as intervertebral discs included in the acquired imaging condition (Step S104).

Then, the display controller 26c controls to display, regarding a plurality of intervertebral discs, the information representing the imaging areas that concern the intervertebral discs of imaging subjects selected by the selector 26b and the information representing the imaging areas that concern the other intervertebral discs in different display forms, on the display 25 (Step S105).

Subsequently, when the receptor 26d receives a selection operation that selects the intervertebral discs of imaging subjects (Yes at Step S106), the selector 26b re-selects the intervertebral discs of imaging subjects in response to the selection operation received by the receptor 26d (Step S104), and the display controller 26c alters the display forms of the information indicative of the imaging areas that concern the respective intervertebral discs in response to the re-selection (Step S105). In this manner, the alteration in display of the information concerning the selection of the intervertebral discs of imaging subjects and the information concerning the imaging areas is repeated while the receptor 26d receives a selection operation that selects the intervertebral discs of imaging subjects.

The controller 26 repeats the receiving of a selection operation of intervertebral discs by the receptor 26d until an instruction to end the defining of imaging areas is received from the operator (No at Step S107). Then, when the controller 26 receives an instruction to end the defining of imaging areas (No at Step S106 and Yes at Step S107), the selector 26b notifies the imaging controller 26e of the imaging areas that concern the intervertebral discs of imaging subjects being selected at that time. Consequently, the data collection of the imaging areas that concern the intervertebral discs of imaging subjects is performed by the imaging controller 26e.

As in the foregoing, according to the MRI apparatus 100 in the first embodiment, regarding a plurality of detected intervertebral discs, the information representing the imaging areas that concern the intervertebral discs of imaging subjects and the information representing the imaging areas that concern the other intervertebral discs are displayed in different display forms on the display. This enables the operator to easily select the intervertebral discs intended to be the imaging subjects. Furthermore, in the examination in which intervertebral discs are imaged, the time and effort of the operator in defining the imaging areas can be reduced, whereby the examination throughput can be improved.

Second Embodiment

Next, a second embodiment will be described. In the second embodiment, a situation of complementing intervertebral discs that have failed to be detected will be exemplified. While the configuration of an MRI apparatus according to the second embodiment is basically the same as those illustrated in FIGS. 1 and 2, the processing performed by the detector 26a is different. For this reason, the following is described with a focus on the processing performed by the detector 26a in the second embodiment.

The detector 26a in the second embodiment calculates the length of the interval of intervertebral discs for each pair of adjacent intervertebral discs included in a plurality of intervertebral discs and, when a pair the calculated length of which is greater than a reference value is present, performs the processing of further detecting the intervertebral disc information that corresponds to a position between the intervertebral discs of the pair.

Figure 6:
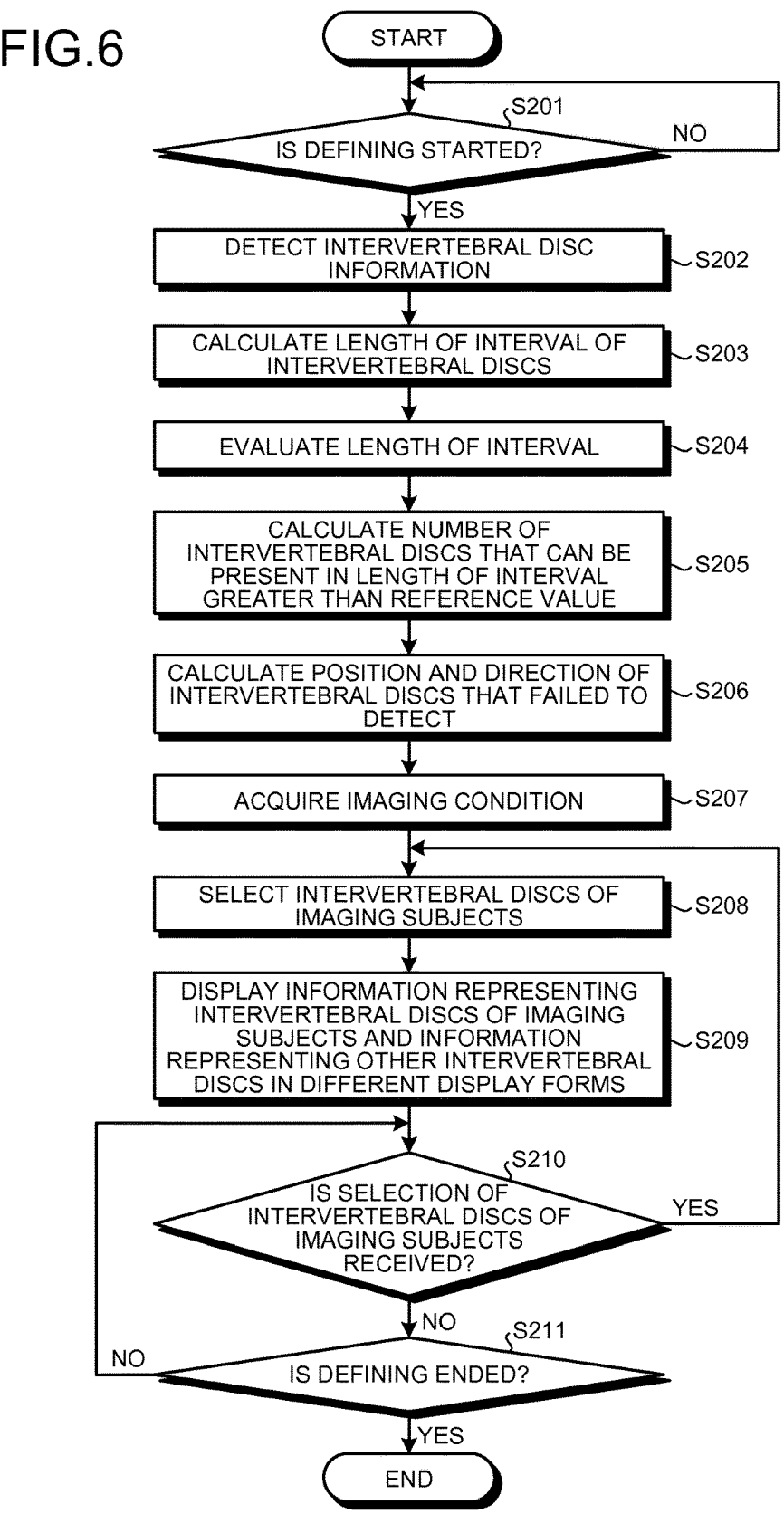
FIG. 6 is a flowchart illustrating a processing procedure of an imaging-area defining method performed by an MRI apparatus according to a second embodiment.

FIG. 6 is a flowchart illustrating a processing procedure of an imaging-area defining method performed by the MRI apparatus 100 in the second embodiment. As illustrated in FIG. 6, in the MRI apparatus 100 in the second embodiment, the controller 26 starts the following processing when an instruction to start defining imaging areas is received from the operator (Yes at Step S201).

The detector 26a first detects, based on an image in which the spine of a subject is imaged, the intervertebral disc information indicative of the position and direction of each intervertebral disc for each of a plurality of intervertebral discs (Step S202). Thereafter, the detector 26a calculates the length of the interval of intervertebral discs based on the detected intervertebral disc information (Step S203). At this time, the detector 26a smoothly connects the respective positions of the detected intervertebral discs with a fitted curve, by using spline interpolation and the like, for example. The detector 26a then calculates the length of the interval of intervertebral discs for each pair of adjacent intervertebral discs, along the fitted curve.

Subsequently, the detector 26a evaluates the length of the calculated interval based on a predetermined reference value, for each pair of adjacent intervertebral discs (Step S204). At this time, the detector 26a compares the length of the calculated interval with the reference value and determines if there is a pair the interval of which is greater than the reference value, for each pair of adjacent intervertebral discs, for example.

If there is a pair having been determined to have the length of the interval greater than the reference value, the detector 26a then calculates the number of intervertebral discs that can be present within the interval of the pair (Step S205). At this time, the detector 26a calculates an average value of the lengths of the intervals of the pairs having been determined to have the length of the interval below the reference value, for example. The detector 26a then divides the length of the interval of the pair having been determined to have the length of the interval greater than the reference value, by the calculated average value, and defines the quotient thereof as the number of intervertebral discs that can be present within the interval.

Subsequently, the detector 26a calculates the positions and directions of the intervertebral discs that have failed to be detected (Step S206). At this time, the detector 26a divides the fitted curve into the number of calculated intervertebral discs, and calculates the positions of divided boundaries as "positions of intervertebral discs that have failed to be detected," for example. The detector 26a further calculates the directions of planes that are orthogonal to the fitted curve at the positions of divided boundaries as "directions of intervertebral discs that have failed to be detected." The detector 26a then causes the intervertebral-disc information storage 23b to further store therein the information indicative of the calculated positions and directions. The intervertebral disc information indicative of the positions and directions of the intervertebral discs that have failed to be detected can thus be detected.

Thereafter, the selector 26b acquires an imaging condition stored by the imaging-condition storage 23c (Step S207), and selects as many intervertebral discs of imaging subjects as intervertebral discs included in the acquired imaging condition (Step S208).

Then, the display controller 26c controls to display, regarding a plurality of intervertebral discs, the information representing the imaging areas that concern the intervertebral discs of imaging subjects selected by the selector 26b and the information representing the imaging areas that concern the other intervertebral discs in different display forms, on the display 25 (Step S209).

Subsequently, when the receptor 26d receives a selection operation that selects the intervertebral discs of imaging subjects (Yes at Step S210), the selector 26b re-selects the intervertebral discs of imaging subjects in response to the selection operation received by the receptor 26d (Step S208), and the display controller 26c alters the display forms of the information indicative of the imaging areas that concern the respective intervertebral discs in response to the re-selection (Step S209). In this manner, the alteration in display of the information concerning the selection of the intervertebral discs of imaging subjects and the information concerning the imaging areas is repeated while the receptor 26d receives a selection operation that selects the intervertebral discs of imaging subjects.

The controller 26 repeats the receiving of a selection operation of intervertebral discs by the receptor 26d until an instruction to end the defining of imaging areas is received from the operator (No at Step S211). Then, when the controller 26 receives an instruction to end the defining of imaging areas (No at Step S210 and Yes at Step S211), the selector 26b notifies the imaging controller 26e of the imaging areas that concern the intervertebral discs of imaging subjects being selected at that time. Consequently, the data collection of the imaging areas that concern the intervertebral discs of imaging subjects is performed by the imaging controller 26e.

Figure 7:
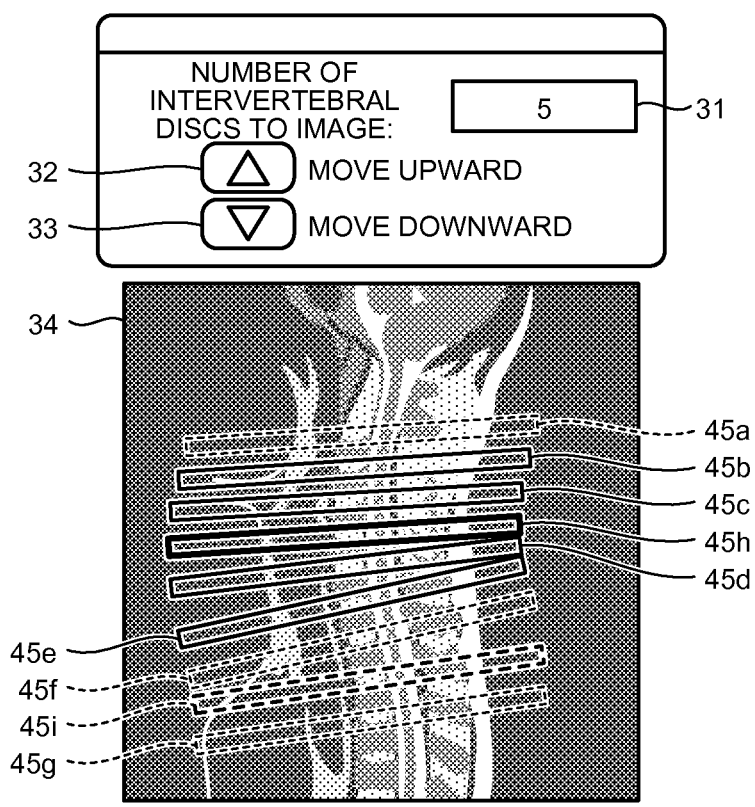
FIG. 7 is a diagram illustrating one example of the display of imaging areas performed by a display controller in the second embodiment.

FIG. 7 is a diagram illustrating one example of the display of imaging areas performed by the display controller 26c in the second embodiment. For example, as illustrated in FIG. 7, the display controller 26c controls to display, in the same manner as in the example illustrated in FIG. 3, the text box 31, the button 32, the button 33, and the positioning sagittal image 34. The display controller 26c further controls to display the imaging areas that concern the respective intervertebral discs with rectangular graphics on the positioning sagittal image 34. In FIG. 7, illustrated is an example of a situation that the number of intervertebral discs is five.

It is assumed here that, by the detector 26a, the intervertebral disc information about the respective intervertebral discs corresponding to graphics 45a to 45g illustrated in FIG. 7 has been detected, based on an image in which the spine of a subject is imaged, and the intervertebral disc information about the respective intervertebral discs corresponding to graphics 45h and 45i has subsequently been detected as the intervertebral disc information about the intervertebral discs that have failed to be detected, for example. It is further assumed that, by the selector 26b, out of the respective intervertebral discs corresponding to the graphics 45a to 45i illustrated in FIG. 7, the respective intervertebral discs corresponding to the graphics 45b to 45d and 45h have been selected as the intervertebral discs of imaging subjects, for example.

In this case, the display controller 26c controls to display, out of a plurality of intervertebral discs, the graphics 45b to 45e that concern the intervertebral discs of imaging subjects and the graphics 45a, 45f, 45g, and 45i that concern the other intervertebral discs that are not the imaging subjects in different display forms. Furthermore, out of the intervertebral discs of imaging subjects, the display controller 26c controls to display the graphics 45b to 45d that concern the intervertebral discs that have been detected based on the image in which the spine of the subject is imaged, and the graphic 45h that concerns the intervertebral disc that has been added as the intervertebral disc that has failed to be detected in different display forms. Moreover, out of the intervertebral discs that are not the imaging subjects, the display controller 26c controls to display the graphics 45a, 45f, and 45g that concern the intervertebral discs that have been detected based on the image in which the spine of the subject is imaged, and the graphic 45i that concerns the intervertebral disc that has been added as the intervertebral disc that has failed to be detected in different display forms.

At this time, as illustrated in FIG. 7, the display controller 26c alters the line style (such as solid lines and dotted lines) of the graphics 45b to 45e, and the graphics 45a, 45f, 45g, and 45i, for example. The display controller 26c further alters the line width of the graphics 45b to 45d and the graphic 45h, and alters also the line width of the graphics 45a, 45f, 45g, and 45i.

As in the foregoing, according to the MRI apparatus 100 in the second embodiment, the intervertebral discs that have failed to be detected can be complemented automatically, whereby the time and effort of the operator to manually add imaging areas can be reduced.

In the above-described second embodiment, a situation has been exemplified in which the detector 26a evaluates the length of the interval of intervertebral discs by using a predetermined reference value. The embodiment, however, is not limited to this. For example, the detector 26a may use the length of the interval of intervertebral discs calculated based on the body height of the subject as the reference value. In that case, the detector 26a refers to the patient information stored in the patient-information storage 23d and acquires the body height of the subject, for example. The detector 26a then calculates the suitable length of the interval of intervertebral discs for the acquired body height by using a computational expression predefined based on an anatomical standpoint, and uses the calculated length of the interval as the reference value, for example.

Third Embodiment

Next, a third embodiment will be described. In the third embodiment, a situation that intervertebral discs, in which the length of the interval of adjacent intervertebral discs in a plurality of detected imaging areas is small, are excluded from imaging subjects will be exemplified. While the configuration of an MRI apparatus according to the third embodiment is basically the same as those illustrated in FIGS. 1 and 2, the processing performed by the selector 26b is different. For this reason, the following is described with a focus on the processing performed by the selector 26b in the third embodiment.

The selector 26b in the third embodiment, at the time of selecting the intervertebral discs of imaging subjects, selects the intervertebral discs out of a plurality of intervertebral discs such that the length of the interval of adjacent intervertebral discs is to be greater than a reference value.

Figure 8:
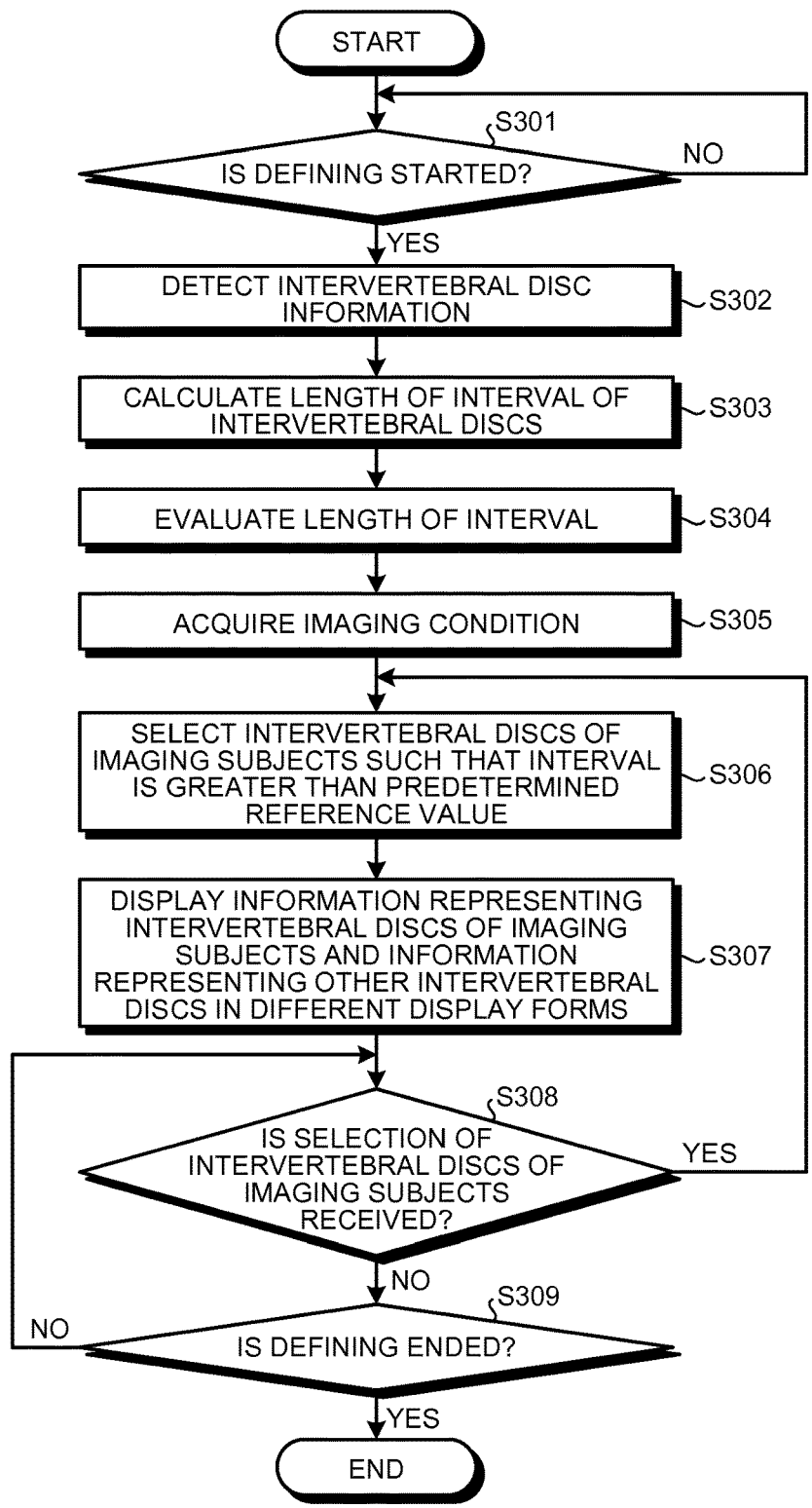
FIG. 8 is a flowchart illustrating a processing procedure of an imaging-area defining method performed by an MRI apparatus according to a third embodiment.

FIG. 8 is a flowchart illustrating a processing procedure of an imaging-area defining method performed by the MRI apparatus 100 in the third embodiment. As illustrated in FIG. 8, in the MRI apparatus 100 in the third embodiment, the controller 26 starts the following processing when an instruction to start defining imaging areas is received from the operator (Yes at Step S301).

The detector 26a first detects, based on an image in which the spine of a subject is imaged, the intervertebral disc information indicative of the position and direction of each intervertebral disc for each of a plurality of intervertebral discs (Step S302). Thereafter, the detector 26a calculates the length of the interval of intervertebral discs based on the detected intervertebral disc information (Step S303). At this time, the detector 26a calculates the length of the interval of intervertebral discs for each pair of adjacent intervertebral discs in the same method as described in the second embodiment, for example.

Subsequently, the detector 26a evaluates the length of the calculated interval based on a predetermined reference value, for each pair of adjacent intervertebral discs (Step S304). At this time, the detector 26a compares the length of the calculated interval with the reference value and determines if there is a pair the interval of which is greater than the reference value, for each pair of adjacent intervertebral discs, for example.

Thereafter, the selector 26b acquires an imaging condition stored by the imaging-condition storage 23c (Step S305), and selects as many intervertebral discs of imaging subjects as the intervertebral discs included in the acquired imaging condition such that the interval is greater than the predetermined reference value (Step S306). At this time, based on the intervertebral disc that is positioned at the uppermost side out of the intervertebral discs selected as imaging subjects, the selector 26b selects downward, including that intervertebral disc, as many intervertebral discs of imaging subjects as the intervertebral discs included in the imaging condition with an interval that is greater than the reference value. As a result, the selector 26b is to select the intervertebral discs out of a plurality of intervertebral discs such that the length of the interval of adjacent intervertebral discs is greater than the reference value.

Then, the display controller 26c controls to display, regarding a plurality of intervertebral discs, the information representing the imaging areas that concern the intervertebral discs of imaging subjects selected by the selector 26b and the information representing the imaging areas that concern the other intervertebral discs in different display forms, on the display 25 (Step S307).

Subsequently, when the receptor 26d receives a selection operation that selects the intervertebral discs of imaging subjects (Yes at Step S308), the selector 26b re-selects the intervertebral discs of imaging subjects in response to the selection operation received by the receptor 26d (Step S306), and the display controller 26c alters the display forms of the information indicative of imaging areas that concern the respective intervertebral discs in response to the re-selection (Step S307). In this manner, the alteration in display of the information concerning the selection of the intervertebral discs of imaging subjects and the information concerning the imaging areas is repeated while the receptor 26d receives a selection operation that selects the intervertebral discs of imaging subjects.

The controller 26 repeats the receiving of a selection operation of intervertebral discs by the receptor 26d until an instruction to end the defining of the imaging areas is received from the operator (No at Step S309). Then, when the controller 26 receives an instruction to end the defining of the imaging areas (No at Step S308 and Yes at Step S309), the selector 26b notifies the imaging controller 26e of the imaging areas that concern the intervertebral discs of imaging subjects being selected at that time. Consequently, the data collection of the imaging areas that concern the intervertebral discs of imaging subjects is performed by the imaging controller 26e.

Figure 9:
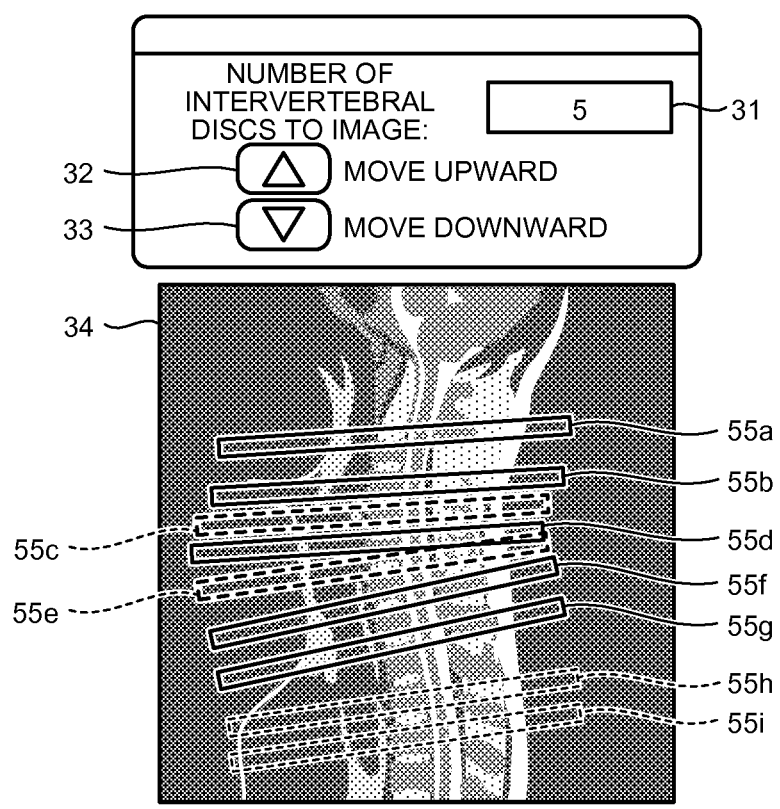
FIG. 9 is a diagram illustrating one example of the display of imaging areas performed by a display controller in the third embodiment.

FIG. 9 is a diagram illustrating one example of the display of imaging areas performed by the display controller 26c in the third embodiment. For example, as illustrated in FIG. 9, the display controller 26c controls to display, in the same manner as in the example illustrated in FIG. 3, the text box 31, the button 32, the button 33, and the positioning sagittal image 34. The display controller 26c further controls to display the imaging areas that concern the respective intervertebral discs with rectangular graphics on the positioning sagittal image 34. In FIG. 9, illustrated is an example of a situation that the number of intervertebral discs of imaging subjects is five.

It is assumed here that, by the detector 26a, the intervertebral disc information about the respective intervertebral discs corresponding to graphics 55a to 55i illustrated in FIG. 9 has been detected, based on an image in which the spine of a subject is imaged, for example. It is further assumed that, by the selector 26b, out of the respective intervertebral discs corresponding to the graphics 55a to 55i illustrated in FIG. 9, the respective intervertebral discs corresponding to the graphics 55a, 55b, 55d, 55f, and 55g have been selected as the intervertebral discs of imaging subjects and the respective intervertebral discs corresponding to the graphics 55c and 55e have been excluded from the subject of selection, for example.

In this case, the display controller 26c controls to display, out of a plurality of intervertebral discs, the graphics 55a, 55b, 55d, 55f, and 55g that concern the intervertebral discs of imaging subjects, and the graphics 55c, 55e, 55h, and 55i that concern the other intervertebral discs that are not the imaging subjects in different display forms. Furthermore, the display controller 26c controls to display, out of the intervertebral discs that are not the imaging subjects, the graphics 55c and 55e that concern the intervertebral discs that have been excluded from the imaging subjects by the selector 26b and the graphics 55h and 55i that concern the other intervertebral discs in different display forms.

At this time, as illustrated in FIG. 9, the display controller 26c alters the line style (such as solid lines and dotted lines) of the graphics 55a, 55b, 55d, 55f, and 55g, and the graphics 55c, 55e, 55h, and 55i, for example. The display controller 26c further alters the line width of the graphics 55c and 55e, and the graphics 55h and 55i.

Figure 10:
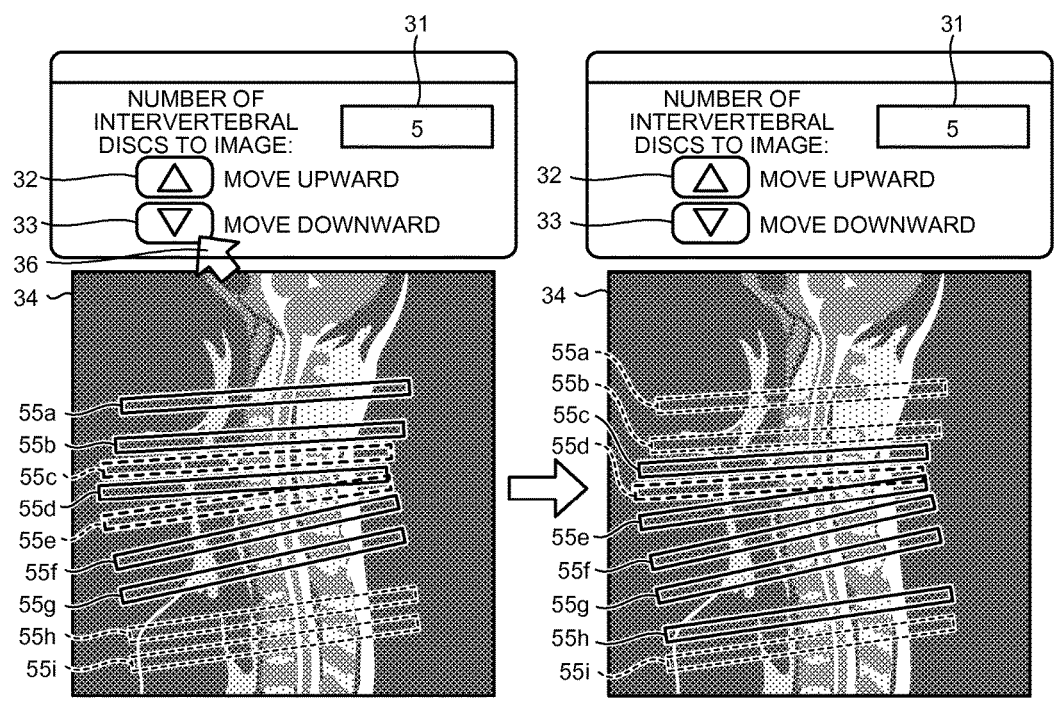
FIG. 10 is a diagram for explaining the re-selection of intervertebral discs performed by a selector and a receptor in the third embodiment.

FIG. 10 is a diagram for explaining the re-selection of intervertebral discs performed by the selector 26b and the receptor 26d in the third embodiment. The text box 31, the buttons 32 and 33, the positioning sagittal image 34, and the graphics 55a to 55i illustrated in FIG. 10 are the same as those illustrated in FIG. 9. For example, as illustrated in FIG. 10, the receptor 26d receives an operation of specifying the button 32 or 33 displayed on the display 25 with the mouse pointer 36 and the like.

When the button 33 (move downward) is specified in a state illustrated on the left-hand side in FIG. 10, the selector 26b newly selects, toward the upper side, only five intervertebral discs of imaging subjects, which is the same as the number of intervertebral discs having been selected as the imaging subjects before the button 33 is specified, including the intervertebral disc corresponding to the graphic 55h positioned immediately below the intervertebral discs corresponding to the graphics 55a, 55b, 55d, 55f, and 55g having been selected as the imaging subjects before the button 33 is specified, as illustrated on the right-hand side in FIG. 10, for example. At this time, the selector 26*b* newly selects the intervertebral discs of imaging subjects with an interval that is greater than the reference value. As a result of this, as illustrated on the right-hand side in FIG. 10, the respective intervertebral discs corresponding to the graphics 55*c* and 55*e* to 55*h* are newly selected as the imaging subjects. Along with this, the display controller 26*c* then controls to display, in display forms indicative of being the imaging subjects, the graphics 55*c* and 55*e* to 55*h* that concern the newly selected intervertebral discs as the imaging subjects, and controls to display, in display forms indicative of not being the imaging subjects, the graphics 55*a*, 55*b*, 55*d*, and 55*i* that concern the other intervertebral discs. The selector 26*b* and the display controller 26*c* perform the same processing each time the button 33 is specified by the operator. Consequently, each time the button 33 is specified by the operator, the intervertebral discs selected as the subject of selection with an interval that is greater than the reference value are to move downward while keeping the number thereof constant.

Meanwhile, when the button 32 (move upward) is specified in a state illustrated on the right-hand side in FIG. 10, the selector 26*b* newly selects, toward the upper side, only five intervertebral discs of imaging subjects, which is the same as the number of intervertebral discs having been selected as the imaging subjects before the button 32 is specified, including the intervertebral disc corresponding to the graphic 55*b* positioned immediately above the intervertebral discs corresponding to the graphics 55*c* and 55*e* to 55*h* having been selected as the imaging subjects before the button 32 is specified, for example. As a result of this, the respective intervertebral discs corresponding to the graphics 55*b*, 55*d*, 55*f*, 55*g*, and 55*h* are newly selected as the imaging subjects, for example. Along with this, the display controller 26*c* then controls to display, in display forms indicative of being the imaging subjects, the graphics 55*b*, 55*d*, 55*f*, 55*g*, and 55*h* that concern the newly selected intervertebral discs as the imaging subjects, and controls to display, in display forms indicative of not being the imaging subjects, the graphics 55*a*, 55*c*, 55*e*, and 55*i* that concern the other intervertebral discs. The selector 26*b* and the display controller 26*c* perform the same processing each time the button 32 is specified by the operator. Consequently, each time the button 32 is specified by the operator, the intervertebral discs selected as the subject of selection with an interval that is greater than the reference value are to move upward while keeping the number thereof constant.

As in the foregoing, according to the MRI apparatus 100 in the third embodiment, an intervertebral disc for which the length of the interval with an adjacent intervertebral disc is small in a plurality of detected imaging areas is automatically excluded from the imaging subjects, whereby the time and effort of the operator to manually adjust the intervals of the imaging areas can be reduced.

In the above-described third embodiment, a situation has been exemplified in which the selector 26*b* selects the intervertebral discs of imaging subjects such that the intervals are to be greater than the predetermined reference value. The embodiment, however, is not limited to this. For example, the selector 26*b* may use the length of the interval of intervertebral discs calculated based on the body height of the subject as the reference value. In that case, the selector 26*b* refers to the patient information stored in the patient-information storage 23*d* and acquires the body height of the subject, for example. The selector 26*b* then calculates the suitable length of the interval of intervertebral discs for the acquired body height by using a computational expression predefined based on an anatomical standpoint, and uses the calculated length of the interval as the reference value, for example.

Fourth Embodiment

Next, a fourth embodiment will be described. In the fourth embodiment, a situation of avoiding the overlap of imaging areas in a plurality of detected imaging areas will be exemplified. While the configuration of an MRI apparatus according to the fourth embodiment is basically the same as those illustrated in FIGS. 1 and 2, the processing performed by the imaging controller 26*e* is different. For this reason, the following is described with a focus on the processing performed by the imaging controller 26*e* in the fourth embodiment.

The imaging controller 26*e* in the fourth embodiment detects, based on the intervertebral disc information detected by the detector 26*a*, the overlap of imaging areas that concern the intervertebral discs of imaging subjects selected by the selector 26*b* and, when an overlap is detected, rotates the imaging areas that concern the intervertebral discs of imaging subjects so as to eliminate the overlap.

Figure 11:
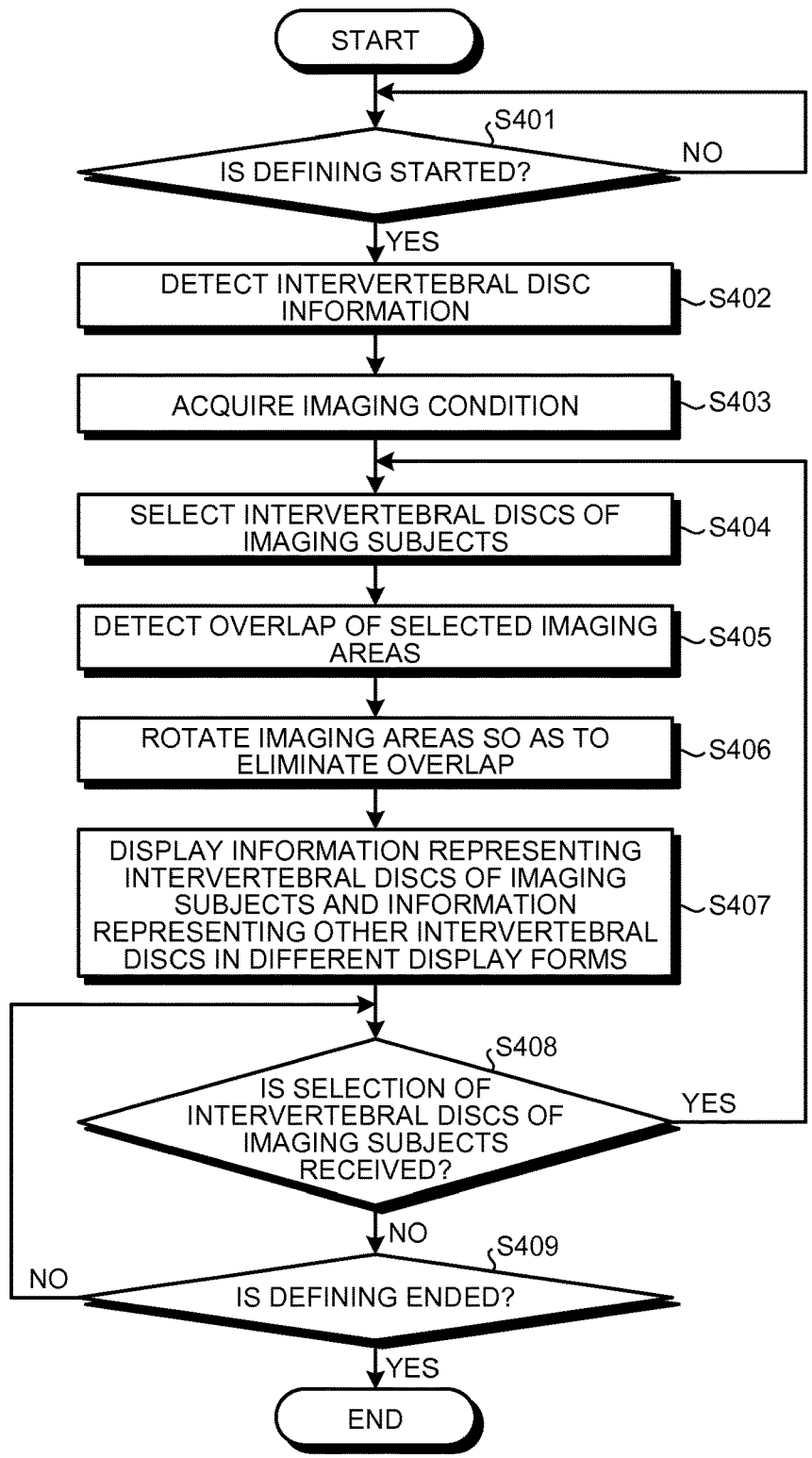
FIG. 11 is a flowchart illustrating a processing procedure of an imaging-area defining method performed by an MRI apparatus according to a fourth embodiment.

FIG. 11 is a flowchart illustrating a processing procedure of an imaging-area defining method performed by the MRI apparatus 100 in the fourth embodiment. As illustrated in FIG. 11, in the MRI apparatus 100 in the fourth embodiment, the controller 26 starts the following processing when an instruction to start defining imaging areas is received from the operator (Yes at Step S401).

The detector 26*a* first detects, based on an image in which the spine of a subject is imaged, the intervertebral disc information indicative of the position and direction of each intervertebral disc for each of a plurality of intervertebral discs (Step S402). Thereafter, the selector 26*b* acquires an imaging condition stored by the imaging-condition storage 23*c* (Step S403), and selects as many intervertebral discs of imaging subjects as the intervertebral discs included in the acquired imaging condition (Step S404).

Subsequently, the imaging controller 26*e* detects an overlap of imaging areas that concern the intervertebral discs selected by the selector 26*b* (Step S405). At this time, the imaging controller 26*e* acquires an imaging condition stored by the imaging-condition storage 23*c* and, based on the length, width, and thickness of the imaging areas included in the acquired imaging condition, and on the intervertebral disc information indicative of the position and direction of the intervertebral discs selected by the selector 26*b*, detects the overlap of the imaging areas that concern the intervertebral discs of imaging subjects, for example.

When the overlap of the imaging areas of the intervertebral discs of imaging subjects is detected, the imaging controller 26*e* then rotates the imaging areas that concern the intervertebral discs of imaging subjects so as to eliminate the overlap (Step S406).

Then, the display controller 26*c* controls to display, regarding a plurality of intervertebral discs, the information representing the imaging areas that concern the intervertebral discs of imaging subjects selected by the selector 26*b* and the information representing the imaging areas that concern the other intervertebral discs in different display forms, on the display 25 (Step S407).

Subsequently, when the receptor 26*d* receives a selection operation that selects the intervertebral discs of imaging subjects (Yes at Step S408), the selector 26*b* re-selects the intervertebral discs of imaging subjects in response to the selection operation received by the receptor 26*d* (Step S404). Thereafter, the imaging controller 26e detects an overlap of the imaging areas that concern the intervertebral discs of imaging subjects again (Step S405), and rotates the imaging areas so as to eliminate the overlap (Step S406). The display controller 26c, in response to this, alters the display forms of the information indicative of the imaging areas that concern the respective intervertebral discs (Step S407). In this manner, the alteration in the display of the information concerning the selection of the intervertebral discs of imaging subjects and the information concerning the imaging areas is repeated while the receptor 26d receives a selection operation that selects the intervertebral discs of imaging subjects.

The controller 26 repeats the receiving of a selection operation of intervertebral discs by the receptor 26d until an instruction to end the defining of the imaging areas is received from the operator (No at Step S409). Then, when the controller 26 receives an instruction to end the defining of the imaging areas (No at Step S408 and Yes at Step S409), the selector 26b notifies the imaging controller 26e of the imaging areas that concern the intervertebral discs of imaging subjects being selected at that time. Consequently, the data collection of the imaging areas that concern the intervertebral discs of imaging subjects is performed by the imaging controller 26e.

Figure 12:
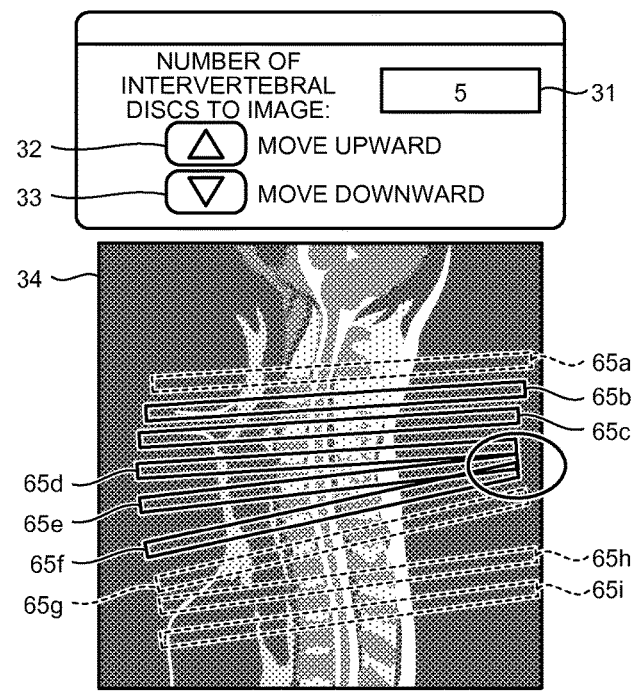
FIGS. 12 and 13 are diagrams for explaining the detection of an overlap of imaging areas performed by an imaging controller in the fourth embodiment.
Figure 13:
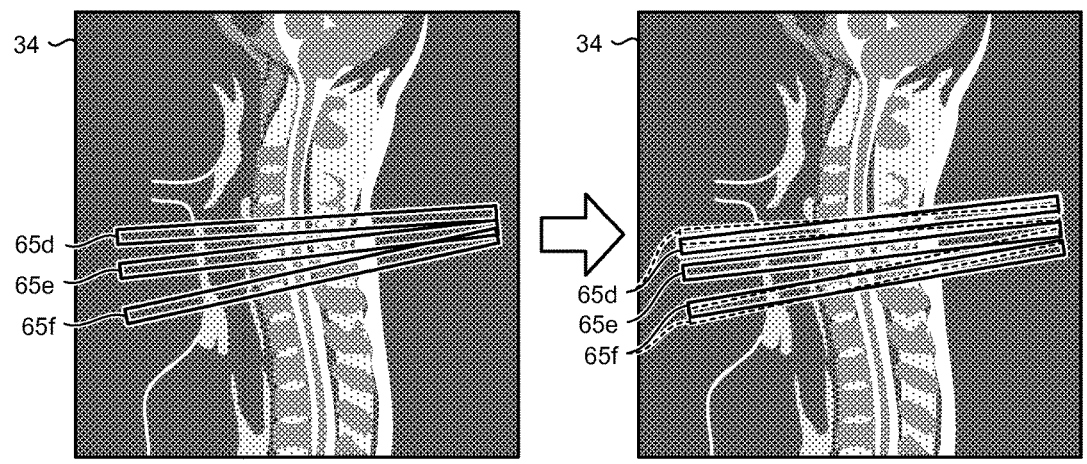

FIGS. 12 and 13 are diagrams for explaining the detection of the overlap of imaging areas performed by the imaging controller 26e in the fourth embodiment. It is assumed here that, by the detector 26a, the intervertebral disc information about respective intervertebral discs corresponding to graphics 65a to 65i illustrated in FIG. 12 has been detected, based on an image in which the spine of a subject is imaged, for example. It is further assumed that, by the selector 26b, out of the respective intervertebral discs corresponding to the graphics 65a to 65i illustrated in FIG. 12, the respective intervertebral discs corresponding to the graphics 65b to 65f have been selected as the intervertebral discs of imaging subjects, for example.

It is assumed that, out of the respective intervertebral discs corresponding to the graphics 65b to 65f selected as imaging subjects, as indicated inside an ellipse illustrated in FIG. 12, the imaging area of the intervertebral disc corresponding to the graphic 65d and the imaging area of the intervertebral disc corresponding to the graphic 65e are overlapped and the imaging area of the intervertebral disc corresponding to the graphic 65e and the imaging area of the intervertebral disc corresponding to the graphic 65f are overlapped, for example.

In this case, as illustrated in FIG. 13, the imaging controller 26e rotates each of the imaging area of the intervertebral disc corresponding to the graphic 65d and the imaging area of the intervertebral disc corresponding to the graphic 65f, and thereby avoids the overlaps having occurred in the respective imaging areas. For example, the imaging controller 26e rotates one or both of the imaging areas such that the angle formed by the planes of two overlapping imaging areas becomes smaller. At this time, it is desirable that the imaging controller 26e rotate the imaging areas within a range that the intervertebral disc falls into the thickness of the imaging area. For example, the imaging controller 26e rotates the imaging area within a predetermined range.

For example, the imaging controller 26e defines, as a reference imaging area, the imaging area that concerns the intervertebral disc positioned in the middle of the intervertebral discs of imaging subjects selected by the selector 26b. At this time, if an even number of the intervertebral discs of imaging subjects is present, the imaging controller 26e defines, as the reference imaging area, either one of two imaging areas positioned near the middle. Then, when the reference imaging area and the imaging area next thereto are overlapped, the imaging controller 26e obtains a rotation angle to eliminate the overlap.

Figure 14:
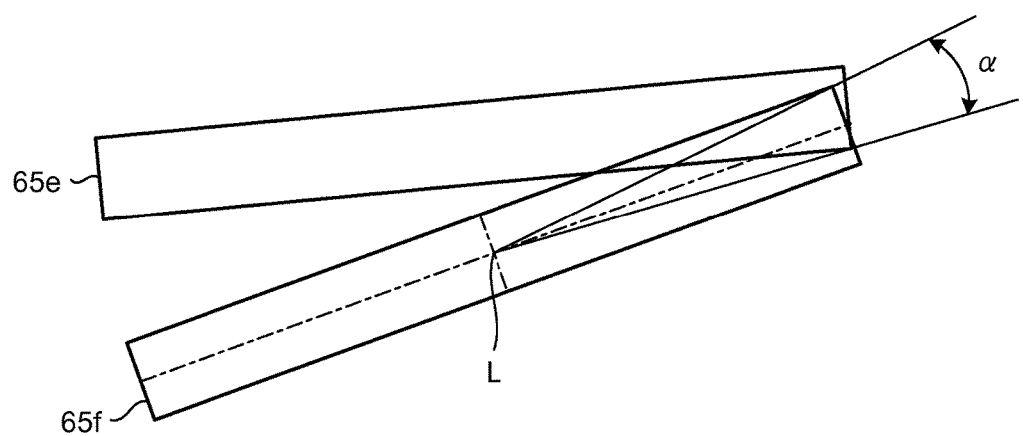
FIGS. 14 and 15 are diagrams for explaining the rotation of imaging areas performed by the imaging controller in the fourth embodiment.
Figure 15:
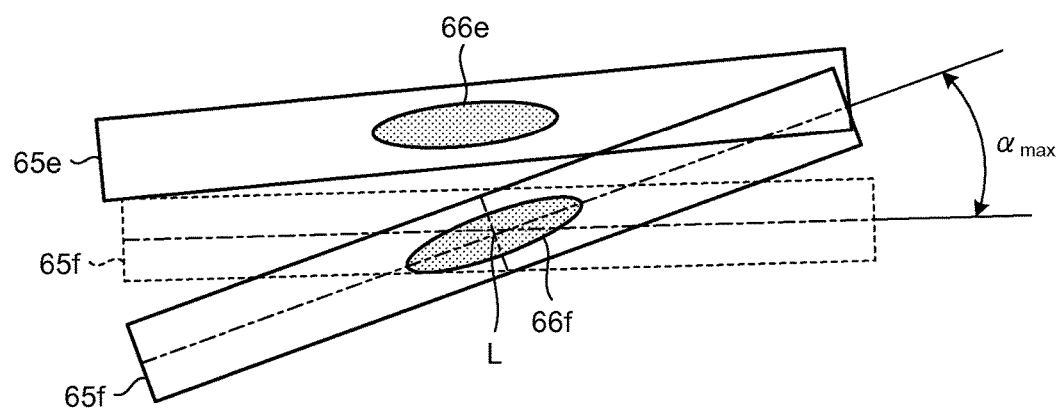

FIGS. 14 and 15 are diagrams for explaining the rotation of the imaging areas performed by the imaging controller 26e in the fourth embodiment. For example, as illustrated in FIG. 14, when an imaging area 65e and an imaging area 65f are overlapped, the imaging controller 26e defines the imaging area 65e as the reference imaging area. The imaging controller 26e then rotates the imaging area 65f that is not the reference imaging area, and thereby avoids the overlap of the imaging area 65e and the imaging area 65f. The imaging controller 26e first obtains an outer product A×B of a vector A in the longitudinal direction of the imaging area 65f and a vector B in the thickness direction thereof, and thereby obtains a rotation axis L of the imaging area 65f. Furthermore, the imaging controller 26e calculates an angle to rotate the imaging area 65f at the obtained rotation axis L. At this time, as illustrated in FIG. 14, the imaging controller 26e calculates a smallest rotation angle α at which the overlap of the imaging area 65e and the imaging area 65f is eliminated. The imaging controller 26e then rotates the imaging area 65f only by the calculated rotation angle α. The imaging controller 26e repeats this processing the same number of times as the number of overlapping imaging areas.

For example, as illustrated in FIG. 15, when the imaging area 65e concerning an intervertebral disc 66e and the imaging area 65f concerning an intervertebral disc 66f are overlapped, the rotation angle of the imaging area 65f can be further increased from α until the outer edge of the imaging area 65f is brought into contact with the outer edge of the imaging area 65e. Consequently, the imaging controller 26e calculates a rotation angle $α_{max}$ at which the outer edge of the imaging area 65f on the side not overlapping the imaging area 65e and the imaging area 65e are brought into contact. The imaging controller 26e then rotates the imaging area 65f in a range from α to $α_{max}$ so as not to overlap with the other imaging area. At this time, it is desirable that the imaging controller 26e rotate the imaging area 65f within a range that the intervertebral disc 66f falls into the thickness of the imaging area 65f.

As in the foregoing, in the fourth embodiment, the overlap of imaging areas in a plurality of detected imaging areas can be avoided automatically, whereby the time and effort of the operator to manually adjust the imaging areas so as to eliminate the overlap of the imaging areas can be reduced. Furthermore, by eliminating the overlap of the imaging areas, the absence of signal due to the overlap can be prevented. That is, the artifact that arises due to the imaging areas being overlapped can be reduced, whereby the image quality of an image obtained by imaging can be improved.

In the above-described fourth embodiment, a situation of avoiding the overlap of imaging areas by rotating the imaging area has been exemplified. The embodiment, however, is not limited to this. For example, the overlapping imaging areas may be imaged at the time interval by altering the order of imaging the imaging areas.

In this case, the imaging controller 26e detects, based on the intervertebral disc information detected by the detector 26a, the overlap of the imaging areas that concern the intervertebral discs of imaging subjects selected by the selector 26b and, when the overlap is detected, alters the order of imaging the imaging areas that concern the intervertebral discs of imaging subjects such that the overlapping imaging areas are imaged at the time interval.

Figure 16:
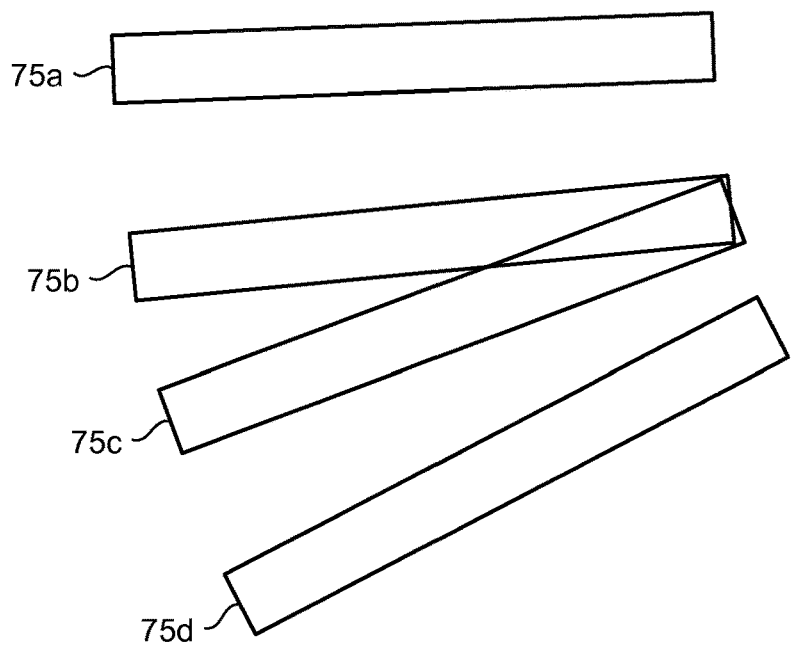
FIGS. 16 and 17 are diagrams for explaining the alteration of the order of imaging performed by the imaging controller in the fourth embodiment.
Figure 17:
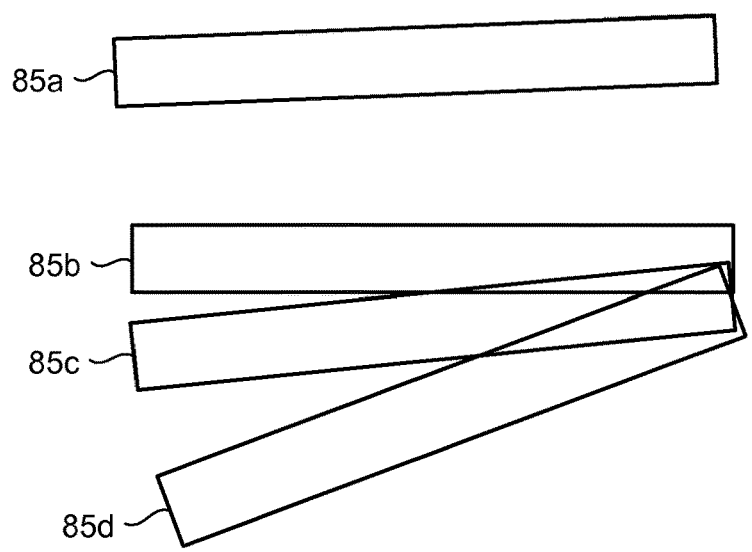

FIGS. 16 and 17 are diagrams for explaining the alteration of the order of imaging performed by the imaging controller 26e in the fourth embodiment. For example, as illustrated in FIG. 16, it is assumed that, out of imaging areas 75a to 75d that concern the intervertebral discs of imaging subjects, the imaging area 75b and the imaging area 75c are overlapped. In this case, the imaging controller 26e images the respective imaging areas in the order of the imaging area 75c, the imaging area 75a, the imaging area 75b, and the imaging area 75d, for example.

Meanwhile, as illustrated in FIG. 17, it is assumed that, out of imaging areas 85a to 85d that concern the intervertebral discs of imaging subjects, the imaging areas 85b to 85d are overlapped, for example. When the imaging areas not overlapping are few as in this case, the imaging controller 26e waits without performing the imaging, or images the other imaging areas not overlapping, for a relaxation time. That is, in this case, the imaging controller 26e, after imaging the respective imaging areas in the order of the imaging area 85c, the imaging area 85a, and the imaging area 85b, waits only a predetermined wait time without performing the imaging, and then images the imaging area 85d, for example. The predetermined wait time here is adjusted depending on the type of pulse sequence and the imaging condition (e.g., a flip angle).

In the above-described fourth embodiment, a situation of automatically avoiding the overlap of imaging areas by the imaging controller 26e has been exemplified. The embodiment, however, is not limited to this. For example, the imaging controller 26e may be configured to receive an operation of rotating an imaging area so as to eliminate the overlap of imaging areas from the operator, and to rotate the imaging area in response to the received operation. In this case, the imaging controller 26e may be configured to control the display 25 to display a message informing the operator that the imaging areas are overlapped, for example.

In the foregoing first to fourth embodiments, a situation has been exemplified in which the selector 26b selects as many intervertebral discs of imaging subjects as the intervertebral discs included in the imaging condition. The embodiment, however, is not limited to this. For example, the selector 26b may be configured to receive an operation of inputting a numerical value in the text box 31 from the operator, and to select as many intervertebral discs of imaging subjects as the received number. Furthermore, the selector 26b may be configured to receive, from the operator, an operation of selecting as an imaging subject an intervertebral disc not selected as the imaging subject and an operation of excluding an intervertebral disc selected as imaging subjects from the imaging subjects and to increase or decrease the intervertebral discs of imaging subjects in response to the received operation, for each intervertebral disc displayed on the display 25. In that case, the imaging controller 26e may be configured to control to display, altering the display forms, the intervertebral discs automatically selected by the selector 26b and the intervertebral discs the operator has manually selected.

In the foregoing first to fourth embodiments, a situation in which the selector 26b selects the intervertebral discs of imaging subjects out of a plurality of intervertebral discs from the upper side, from the lower side, or from near the middle has been exemplified. The embodiment, however, is not limited to this. For example, when the MRI apparatus 100 images the subject in a wide range while moving the couchtop 4a in a continuous manner or in a phased manner, the selector 26b may be configured to select only a predetermined of intervertebral discs of imaging subjects from a position of high field homogeneity. In this case, the selector 26b identifies the position of high field homogeneity based on BO distribution data collected for shimming in preparatory imaging that is performed prior to the actual imaging, for example.

The graphic user interface (GUI) to select the intervertebral discs of imaging subjects is not limited to the text box 31 and the buttons 32 and 33 illustrated in FIG. 3. For example, the specification of the position and the range of selecting the intervertebral discs of imaging subjects may be received from the operator. It may be further configured to receive the specification of the number of slices per intervertebral disc from the operator.

Figure 18:
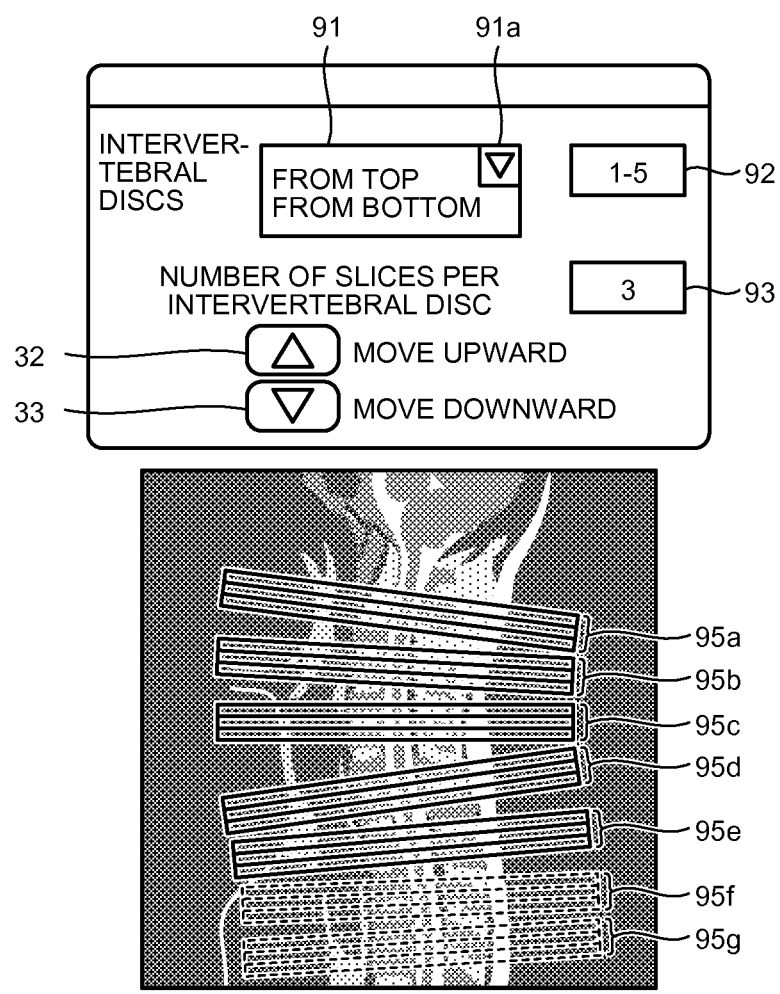
FIG. 18 is a diagram for explaining the selection of intervertebral discs according to modifications in the first to fourth embodiments.

FIG. 18 is a diagram for explaining the selection of intervertebral discs according to modifications in the first to fourth embodiments. For example, as illustrated in FIG. 18, the display controller 26c controls to display, in place of the text box 31 illustrated in FIG. 3, a pull-down menu 91 to specify the position of selecting the intervertebral discs of imaging subjects, and a text box 92 to specify the range of intervertebral discs based on the specified position. When an operation of specifying a button 91a of the pull-down menu 91 is performed by the operator with a mouse pointer and the like, as illustrated in FIG. 18, the display controller 26c controls to display a list including menus of "from the top" and "from the bottom." The display controller 26c further controls to display a text box 93 to specify the number of slices per intervertebral disc.

The receptor 26d then receives, from the operator, an operation of selecting either "from the top" or "from the bottom" from the pull-down menu 91 as the position of selecting the intervertebral discs of imaging subjects. The receptor 26d further receives, from the operator, an operation of inputting the range represented by two numerical values into the text box 92 as the range of intervertebral discs. For example, as illustrated in FIG. 18, the receptor 26d receives an operation of inputting "1-5" that represents a range of one to five. The receptor 26d further receives, from the operator, an operation of specifying a numerical value into the text box 93 as the number of slices per intervertebral disc. For example, as illustrated in FIG. 18, the receptor 26d receives an operation of inputting "3" representing that the number of slices per intervertebral disc is three.

The selector 26b selects, based on the position selected from the pull-down menu 91, the intervertebral discs of the range input to the text box 92 as the intervertebral discs of imaging subjects. For example, as illustrated in FIG. 18, when "from the top" is selected from the pull-down menu 91 and "1-5" is input to the text box 92, the selector 26b selects, out of a plurality of intervertebral discs included in a positioning sagittal image, the first to fifth intervertebral discs counted from the top as the intervertebral discs of imaging subjects.

Along with this, regarding graphics 95a to 95g that concern a plurality of intervertebral discs included in the positioning sagittal image, the display controller 26c controls to display, in display forms indicative of being the imaging subjects, the graphics 95a to 95e that concern the intervertebral discs selected as the imaging subjects, and controls to display the graphics 95f and 95g that concern the other intervertebral discs in display forms indicative of not being the imaging subjects.

The selector 26b re-selects the intervertebral discs of imaging subjects each time the selection of the menu in the pull-down menu 91 or the input of the range in the text box 92 is performed by the operator. The display controller 26c switches the display of the graphics that concern the respective intervertebral discs depending on the intervertebral discs selected by the selector 26b. The operation of the selector 26b and that of the display controller 26c at the time the button 32 or 33 is specified by the operator are the same as those explained in the respective first to fourth embodiments in the foregoing.

Moreover, the display controller 26c alters the shapes of the graphics that concern the intervertebral discs depending on the numerical value input to the text box 93. For example, as the graphics 95a to 95g illustrated in FIG. 18, the display controller 26c controls to display the area within the rectangular graphic by dividing the area in the short direction by the number for which the numerical value is input to the text box 93. When the number of slices per intervertebral disc is changed by the operator, the controller 26 then updates the number of slices within the imaging area, which is included in the imaging condition stored in the imaging-condition storage 23c, to the number after the change.

In the foregoing first to fourth embodiments, a situation in which the detector 26a detects the intervertebral disc information based on the positioning sagittal image has been exemplified. The embodiment, however, is not limited to this. For example, the detector 26a may detect the intervertebral disc information based on a variety of images imaged for diagnosis. That is, a variety of images can be used as long as they include intervertebral discs and the vertebral canal of the subject, or at least intervertebral discs.

The various functions described in the foregoing first to fourth embodiments can be implemented by combining as appropriate. For example, a single MRI apparatus 100 may be provided with all of the functions described in the first to fourth embodiments, or may be provided with the functions of only two or three embodiments. For example, when the MRI apparatus 100 is provided with both functions described in the second embodiment and the third embodiment, on a plurality of intervertebral discs detected, the MRI apparatus 100 can complement the intervertebral discs for the locations for which the length of the interval is large, and at the same time, can exclude the intervertebral discs from the imaging subjects for the locations for which the length of the interval is small. In addition to this, when the MRI apparatus 100 is provided with the function described in the fourth embodiment, the MRI apparatus 100 can further avoid the overlap of imaging areas in the intervertebral discs of imaging subjects.

In the foregoing first to fourth embodiment, a situation in which the intervertebral discs are defined as the target regions has been exemplified. However, vertebral bodies may be defined as the target regions. In that case, the detector 26a detects, based on an image in which the spine of a subject is imaged, vertebral body information indicative of the position and direction of each vertebral body for each of a plurality of vertebral bodies. For example, the detector 26a extracts, as described in the respective first to fourth embodiments, the intervertebral disc information from the image in which the spine of the subject is imaged. The detector 26a then defines the midpoint between the i-th (i being a natural number) and the i+1-th intervertebral discs as the position of a vertebral body. The detector 26a further defines the average of the direction of the i-th and the i+1-th intervertebral discs as the direction of the vertebral body. As for the position and direction of the vertebral bodies located at both ends of the spine, the detector 26a obtains them from the amount of change in the position of and the direction of the other vertebral bodies.

After the vertebral body information is detected by the detector 26a, the various modules that the computer system 20 has perform the same processing by substituting the vertebral bodies for the intervertebral discs. For example, the selector 26b selects the vertebral bodies of imaging subjects out of a plurality of vertebral bodies based on the vertebral body information detected by the detector 26a. The display controller 26c controls to display, regarding a plurality of vertebral bodies the vertebral body information of which has been detected by the detector 26a, the information representing the imaging areas that concern the vertebral bodies of imaging subjects selected by the selector 26b and the information representing the imaging areas that concern the other vertebral bodies in different display forms, on the display 25.

Furthermore, by defining both of the intervertebral discs and the vertebral bodies as the target regions, both may be imaged by one sequence. For example, by defining the imaging area including a plurality of slices so as to include both of intervertebral discs and vertebral bodies, the imaging including both of the intervertebral discs and the vertebral bodies may be repeated by one sequence. Furthermore, by defining the respective imaging areas including a plurality of slices to the intervertebral discs and to the vertebral bodies, each of the imaging including only the intervertebral discs and the imaging including only the vertebral bodies may be performed by one sequence.

According to at least one of the embodiments explained in the foregoing, the operator can easily select the target regions intended to be the imaging subjects.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising processing circuitry configured to:
    detect target region information indicative of a position and a direction of each target region for each of a plurality of target regions included in a spine of a subject based on an image in which the spine is imaged, and when failing to detect a target region at an expected location, calculate a position and a direction of the target region that has failed to be detected, using a detection result of a target region that has been detected successfully, wherein the plurality of target regions include at least intervertebral discs or vertebral bodies; and
    select a set number of target regions as imaging subjects from the plurality of target regions based on the target region information, wherein the set number is determined for each imaging protocol.

2. The magnetic resonance imaging apparatus according to claim 1, wherein the processing circuitry is further configured to:
    detect information indicative of a position and a direction of each intervertebral disc as the target region information for each of a plurality of intervertebral discs when the intervertebral discs are included as target regions; and select intervertebral discs as imaging subjects from the plurality of intervertebral discs.

3. The magnetic resonance imaging apparatus according to claim 1, further comprising
a storage configured to store therein the set number for each imaging protocol,
wherein the processing circuitry is further configured to select the target regions for the set number stored by the storage.

4. The magnetic resonance imaging apparatus according to claim 1, wherein the processing circuitry is further configured to:
receive, from an operator, a selection operation for selecting target regions as imaging subjects; and
newly select target regions as imaging subjects in response to receiving the selection operation.

5. The magnetic resonance imaging apparatus according to claim 4, wherein the processing circuitry is further configured to:
receive an operation specifying one direction or the other direction along a disposed direction of the target regions as the selection operation; and
newly select, when the selection operation is received, as many target regions as imaging subjects as target regions selected as imaging subjects before the selection operation is received, wherein the newly selected target regions include a target region positioned on a side of the direction specified by the selection operation with respect to the target regions selected as imaging subjects before the selection operation is received, and excludes a target region which is selected as an imaging subject before the selection operation is received and which is positioned toward an opposite side to the direction specified by the selection operation.

6. The magnetic resonance imaging apparatus according to claim 1, wherein the processing circuitry is further configured to:
calculate a length of interval of target regions for each pair of adjacent target regions included in the plurality of target regions; and
further detect, when a pair the calculated length of which is greater than a first reference value is present, target region information corresponding to a position between target regions of the pair.

7. The magnetic resonance imaging apparatus according to claim 6, wherein the processing circuitry is further configure to use a length of interval of target regions calculated based on a body height of the subject as the first reference value.

8. The magnetic resonance imaging apparatus according to claim 1, wherein the processing circuitry is further configured to select target regions from the target regions such that a length of interval of adjacent target regions is greater than a second reference value when selecting the target regions as imaging subjects.

9. The magnetic resonance imaging apparatus according to claim 8, wherein the processing circuitry is further configured to use a length of interval of target regions calculated based on a body height of the subject as the second reference value.

10. The magnetic resonance imaging apparatus according to claim 1, wherein the processing circuitry is further configured to:
detect an overlap of imaging areas concerning the selected target regions based on the detected target region information; and
rotate, when an overlap is detected, an imaging area concerning the selected target regions so as to eliminate the overlap.

11. The magnetic resonance imaging apparatus according to claim 1, wherein the processing circuitry is further configured to:
detect an overlap of imaging areas concerning the selected target regions based on the detected target region information; and
alter, when an overlap is detected, an order of imaging the imaging areas concerning the target regions of the imaging subjects such that the overlapping imaging areas are imaged at a time interval.

12. A magnetic resonance imaging apparatus comprising processing circuitry configured to:
detect target region information indicative of a position and a direction of each target region for each of a plurality of target regions included in a spine of a subject based on a magnetic resonance image which includes the spine, wherein the target regions include at least intervertebral discs or vertebral bodies;
select, as imaging subjects, target regions from the plurality of target regions based on the target region information;
cause a display to display, regarding the plurality of target regions, information representing imaging areas that concern the selected target regions and information representing imaging areas that concern other target regions of the plurality of target regions in different display forms; and
receive, from an operator, a selection operation for selecting the target regions as imaging subjects,
wherein the processing circuitry is further configured to:
receive an operation of specifying one direction or the other direction along a disposed direction of the target regions as the selection operation; and
in response to receiving the selection operation, newly selecting target regions as imaging subjects,
wherein the newly selected target regions have a same number of target regions as the selected target regions before the selection operation is received, and
wherein the newly selected target regions include a target region positioned on a side of the direction specified by the selection operation with respect to the target regions selected as imaging subjects before the selection operation is received, and excludes a target region which is selected as an imaging subject before the selection operation is received and which is positioned toward an opposite side to the direction specified by the selection operation.

13. A magnetic resonance imaging apparatus comprising processing circuitry configured to:
detect target region information indicative of a position and a direction of each target region for each of a plurality of target regions included in a spine of a subject based on an image in which the spine is imaged, and when failing to detect a target region at an expected location, calculate a position and a direction of the target region that has failed to be detected, using a detection result of a target region that has been detected successfully, wherein the plurality of target regions include at least intervertebral discs or vertebral bodies; and
select target regions as imaging subjects from the plurality of target regions based on the target region information, wherein the processing circuitry is further configured to:

calculate a length of interval of target regions for each pair of adjacent target regions included in the plurality of target regions; and further detect, when a pair the calculated length of which is greater than a first reference value is present, target region information corresponding to a position between target regions of the pair.

14. A magnetic resonance imaging apparatus comprising processing circuitry configured to:

detect target region information indicative of a position and a direction of each target region for each of a plurality of target regions included in a spine of a subject based on an image in which the spine is imaged, and when failing to detect a target region at an expected location, calculate a position and a direction of the target region that has failed to be detected, using a detection result of a target region that has been detected successfully, wherein the plurality of target regions include at least intervertebral discs or vertebral bodies; and select target regions as imaging subjects from the plurality of target regions based on the target region information, wherein the processing circuitry is further configured to select target regions from the target regions such that a length of interval of adjacent target regions is greater than a second reference value when selecting the target regions as imaging subjects.

15. A magnetic resonance imaging apparatus comprising processing circuitry configured to:

detect target region information indicative of a position and a direction of each target region for each of a plurality of target regions included in a spine of a subject based on an image in which the spine is imaged, and when failing to detect a target region at an expected location, calculate a position and a direction of the target region that has failed to be detected, using a detection result of a target region that has been detected successfully, wherein the plurality of target regions include at least intervertebral discs or vertebral bodies; and select target regions as imaging subjects from the plurality of target regions based on the target region information, wherein the processing circuitry is further configured to:

detect an overlap of imaging areas concerning the selected target regions based on the detected target region information; and rotate, when an overlap is detected, an imaging area concerning the selected target regions so as to eliminate the overlap.

16. A magnetic resonance imaging apparatus comprising processing circuitry configured to:

detect target region information indicative of a position and a direction of each target region for each of a plurality of target regions included in a spine of a subject based on an image in which the spine is imaged, and when failing to detect a target region at an expected location, calculate a position and a direction of the target region that has failed to be detected, using a detection result of a target region that has been detected successfully, wherein the plurality of target regions include at least intervertebral discs or vertebral bodies; and select target regions as imaging subjects from the plurality of target regions based on the target region information, wherein the processing circuitry is further configured to:

detect an overlap of imaging areas concerning the selected target regions based on the detected target region information; and alter, when an overlap is detected, an order of imaging the imaging areas concerning the target regions of the imaging subjects such that the overlapping imaging areas are imaged at a time interval.

* * * * *